(12) United States Patent
Perfetti et al.

(10) Patent No.: US 7,141,240 B2
(45) Date of Patent: Nov. 28, 2006

(54) GLUCOSE-DEPENDENT INSULIN-SECRETING CELLS TRANSFECTED WITH A NUCLEOTIDE SEQUENCE ENCODING GLP-1

(75) Inventors: Riccardo Perfetti, Los Angeles, CA (US); Hongxiang Hui, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 468 days.

(21) Appl. No.: 10/097,230

(22) Filed: Mar. 12, 2002

(65) Prior Publication Data

US 2003/0186436 A1    Oct. 2, 2003

(51) Int. Cl.
*A61K 48/00* (2006.01)
*A01N 63/00* (2006.01)
*C12N 15/63* (2006.01)
*C12N 5/00* (2006.01)
*C12N 5/06* (2006.01)
*C12N 15/85* (2006.01)

(52) U.S. Cl. .................. 424/93.21; 435/325; 435/455

(58) Field of Classification Search ............... 435/455, 435/352, 325, 354, 353, 366, 369, 456, 320.1; 424/93.21; 514/44

See application file for complete search history.

(56) References Cited

U.S. PATENT DOCUMENTS

| | | | |
|---|---|---|---|
| 4,935,000 A | 6/1990 | Dudek | |
| 5,120,712 A | 6/1992 | Habener | |
| 5,219,752 A | 6/1993 | Takazawa et al. | |
| 5,397,706 A | 3/1995 | Correa et al. | |
| 5,512,549 A | 4/1996 | Chen et al. | |
| 5,530,023 A | 6/1996 | Korth | |
| 5,545,618 A | 8/1996 | Buckley et al. | |
| 5,574,008 A | 11/1996 | Johnson et al. | |
| 5,587,309 A | 12/1996 | Rubin et al. | |
| 5,595,722 A | 1/1997 | Grainger et al. | |
| 5,614,492 A | 3/1997 | Habener | |
| 5,631,224 A | 5/1997 | Efendic et al. | |
| 5,654,267 A | 8/1997 | Vuori et al. | |
| 5,665,864 A | 9/1997 | Quaranta et al. | |
| 5,670,360 A | 9/1997 | Thorens | |
| 5,705,483 A | 1/1998 | Galloway et al. | |
| 5,723,333 A | 3/1998 | Levine et al. | |
| 5,744,327 A | 4/1998 | Newgard | |
| 5,747,325 A | 5/1998 | Newgard | |
| 5,773,255 A | 6/1998 | Laurance et al. | |
| 5,792,656 A | 8/1998 | Newgard | |
| 5,804,421 A | 9/1998 | Vinik et al. | |
| 5,811,266 A | 9/1998 | Newgard | |
| 5,837,236 A | 11/1998 | Dinsmore | |
| 5,840,531 A | 11/1998 | Vinik et al. | |
| 5,846,747 A | 12/1998 | Thorens et al. | |
| 5,846,937 A | 12/1998 | Drucker | |
| 5,849,493 A | 12/1998 | Montminy et al. |
| 5,854,292 A | 12/1998 | Ailhaud et al. |
| 5,858,973 A | 1/1999 | Habener et al. |
| 5,861,278 A | 1/1999 | Wong et al. |
| 5,863,555 A | 1/1999 | Heiber et al. |
| 5,880,261 A | 3/1999 | Waeber et al. |
| 5,888,705 A | 3/1999 | Rubin et al. |
| 5,895,785 A | 4/1999 | Korth |
| 5,902,577 A | 5/1999 | Asfari et al. |
| 5,928,942 A | 7/1999 | Brothers |
| 5,948,623 A | 9/1999 | Sosa-Pineda et al. |
| 5,958,909 A | 9/1999 | Habener |
| 5,961,972 A | 10/1999 | Dinsmore |
| 5,977,071 A | 11/1999 | Galloway et al. |
| 5,981,488 A | 11/1999 | Hoffmann |
| 5,993,799 A | 11/1999 | Newgard |
| 5,994,127 A | 11/1999 | Selden et al. |
| 6,001,647 A | 12/1999 | Peck et al. |
| 6,004,775 A | 12/1999 | Shimasaki et al. |
| 6,006,753 A | 12/1999 | Efendic |
| 6,048,724 A | 4/2000 | Selden et al. |
| 6,051,689 A | 4/2000 | Thorens |
| 6,071,697 A | 6/2000 | Sosa-Pineda et al. |
| 6,087,129 A | 7/2000 | Newgard et al. |

(Continued)

FOREIGN PATENT DOCUMENTS

WO          01/39784          6/2001

OTHER PUBLICATIONS

U.S. Appl. No. 60/310,982.*

(Continued)

*Primary Examiner*—Brian Whiteman
(74) *Attorney, Agent, or Firm*—Seth D. Levy; Davis Wright Tremaine LLP

(57) ABSTRACT

Disclosed herein are cells that secrete insulin in a glucose-dependent manner. The cell line comprises insulin-secreting cells that have been transfected with a minigene construct comprising a nucleotide sequence encoding for glucagon-like peptide-1 (GLP-1). In preferred embodiments, the minigene construct is operatively associated with a promoter. The cell line may be used to treat diabetes or other conditions in which delivering insulin in a glucose-dependent manner would be advantageous, to investigate the function and development of pancreatic cells, and to test the efficacy of drugs that stimulate insulin secretion. The cells may be implanted in a mammal, or may be included in a device that resides exterior to the mammal, yet which delivers insulin to the mammal in response to the glucose level of a body fluid in contact therewith. The minigene construct may also be implemented in conjunction with an in vivo gene transfer approach.

24 Claims, 11 Drawing Sheets
(1 of 11 Drawing Sheet(s) Filed in Color)

U.S. PATENT DOCUMENTS

| | | | |
|---|---|---|---|
| 6,110,707 A * | 8/2000 | Newgard et al. | |
| 6,110,743 A | 8/2000 | Levine et al. | |
| 6,114,599 A | 9/2000 | Efrat | |
| 6,127,598 A | 10/2000 | German et al. | |
| 6,132,708 A | 10/2000 | Grompe | |
| 6,133,235 A | 10/2000 | Galloway et al. | |
| 6,153,432 A | 11/2000 | Halvorsen et al. | |
| 6,156,306 A * | 12/2000 | Brownlee et al. | 424/93.21 |
| 6,160,022 A | 12/2000 | Bergeron, Jr. | |
| 6,162,907 A | 12/2000 | Habener | |
| 6,210,960 B1 | 4/2001 | Habener et al. | |
| 6,329,336 B1 | 12/2001 | Bridon et al. | |
| 6,642,003 B1 * | 11/2003 | Perfetti | 435/6 |
| 2004/0002468 A1 * | 1/2004 | Wadsworth et al. | 514/44 |

OTHER PUBLICATIONS

Hanahan, Nature, 315:115-122, 1985.*

Mountain, Trends Biotechnol, 18:119-128, 2000.*

Merriam-Webster's collegiate dictionary, 10th ed., Springfield, Massachusetts, USA, 2001, p. 41.*

Invitrogen life technologies, Catalog No. V900-20, 2001 [online], [retrieved from the Invitrogen website using internet <URL: http://www.invitrogen.com/content/sfs/manuals/psectag2_man.pdf>.*

Hongxiang Hui et al., "Glucagon-Like Peptide 1 Induces Differentiation of Islet Duodenal Homeobox-1—Positive Pancreatic Ductal Cells Into Insulin-Secreting Cells," *Diabetes*, vol. 50, pp. 785-796 (Apr. 2001).

R. Ritzel et al., "Glucagon-Like Peptide 1 Increases SEcretory Burst Mass of Pulsatile Insulin Secretion in Patients with Type 2 Diabetes and Impaired Glucose Tolerance," *Diabetes*, vol. 50, pp. 776-784 (Apr. 2001).

Xiaolin Wang et al., "Glucagon-like peptide-1 Regulates the Beta Cell Transcription Factor, PDX-1, in Insulinoma cells," *Endocrinology*, vol. 140, No. 10, pp. 4904-4907 (1999).

A. Vinik et al., "Induction of Pancreatic Islet Neogenesis," *Hormone and Metabolic Research*, vol. 29, No. 6, pp. 255-322 (Jun. 1997).

KM Narayan et al., "Translation research for chronic disease: the case of diabetes: the case of diabetes," *Diabetes Care*, 23-1794-1978 (2000).

DJ Ducker, "The glucagon-like peptides," *Endocrinology*, 142:521-527 (2001).

B. Thorens and G. Waeber, "Glucagon-like peptide-I and the control of insulin secretion in the normal state and in NIDDM," *Diabetes*, 42:1219-1225 (1993).

MA Nauck et al., "Influence of glucagon-like peptide 1 on fasting glycemia in type 1 diabetic patients treated with insulin after sulfonylurea secondary failure," *Diabetes Care*, 21:1925-1931 (1998).

SY Shieh and MJ Tsai, "Cell-specific and ubiquitous factors are responsible for the enhancer activity of the rate insulin II gene," *J Biol Chem*, 266:16708-16714 (1991).

X. Wang et al., "Glucagon-like peptide-1 regulates the beta cell transcription factor, PDS-1, in insulinoma cells," *Endocrinology*, 140:4904-4907 (1999).

R. Perfetti and P. Merkel, "Glucagon-like peptide-1: a major regulator of pancreatic β-cell function," *European J Endocrinol*, 143:717-725 (2000).

A. Vinik et al., "Induciton of pancreatic islet neogenesis," *Horm Metab Res (Symposium Report)*, 29:278-293 (1997).

MA Nauck et al., "Normalization of fasting hyperglycemia by exogenous glucagon-like peptide-1 [7-36 amide] in type 2 (non-insulin dependent) diabetic patients," *Diabetologia*, 36:741-744 (1993).

C. Orsakov, "Glucagon-like peptide-1, a new hormone of the enteroinsular axis," *Diabetologia*, 35:701-711 (1992).

JJ Holst, "Glucagon-like peptide-1 (GLP-1) a newly discovered GI hormone," *Gastroenterology*, 107:1848-1855 (1994).

MA Hussain and JF Habaner, "Glucagon-like peptide-1 increases glucose-dependent activity of the homeoprotein IDX-1 transactivating domain in pancreatic beta-cells," *Biochemical & Biophysical Research Communications*, 274:616-619 (2000).

CA Leech et al., "Expression of cAMP-regulated guanine nucleotide exchange factors in pancreati beta-cells," *Biochemical & Biophysical Research Communication*, 278:44-47.

J. Buteau et al., "Glucagon-like peptide-1 promotes DNA synthesis, activates phosphatidylinositol 3-kinase and increases transcription factor pancreatic and duodenal homebox gene 1 (PDX-1) DNA binding activity in beta (INS-1)-cells," *Diabetologia*, 42:856-864 (1999).

DA Stoffers et al., "Homeodomain protein IDX-1: A master regulator of pancreas development and insulin gene expression," *Trends Endocrinology Metab*, 8:145:151 (1997).

A: Wilmen et al., "The genomic organization of the human GLP-1 receptor gene," *Exp Clin Endocrinol Diabetes*, 106:299-302 (1998).

G. Teitelman et al., "Cell lineage analysis of pancreatic islet cell development; glucagon and insulin cells arise from catecholaminergic precursor present in the pancreatic duct," *Dev Biol*, 121:454-466 (1987).

R. L. Pictet et al., "An ultrastructural analysis of the developing embryonic pancreas," *Dev Biol*, 29:436-467 (1972).

J. Jonsson et al., "Insulin-promotor factor 1 is required for pancreas development in mice," *Nature*, 371:606-609 (1994).

U. Ahlgren et al., "Independent requirement for ISL1 in formation of pancreatic mesenchyme and islet cells," *Nature*, 385:257-260 (1997).

F. J. Naya et al., "Diabetes, defective pancreatic morphogenesis, and abnormal enteroendocrine differentiation in BETA2/NeuroD-deficient mice," *Genes Dev*, 11:2323-2334 (1997).

A. Sosa-Pineda et al., "The Pax4 gene is essential for differentiation of insulin-producing beta cells in the mammalian pancreas," *Nature*, 386:399-402 (1997).

S. Bonner-Weir et al., "A second pathway for regeneration of adult exocrine and endocrine pancrease—A possible recapitulation of embryonic development," *Diabetes*, 42:1715-1720 (1993).

G. Xu et al., "Exendin-4 stimulates both beta-cell replication and neogenesis, resulting in increased beta-cell mass and improved glucose tolerance in diabetic rats," *Diabetes*, 48:2270-2276 (1999).

Y. Wang et al., "Glucagon-like peptide-1 can reverse the age-related decline in glucose tolerance in rats," *J Clin Invest*, 99:2883-2889 (1997).

E. Elstner et al., "Synergistic decrease of clonal proliferation, induction of differentiation and apoptosis of acute promyelocytic leukemia cells after combined treatment with novel 20-epi vitamin D3 analogs and 9-cis reinoid acid," *J Clin Invest*, 99:349-360 (1997).

D.J. Drucker et al., "Glucagon-like peptides," *Diabetes*, 47:159-169 (1998).

H. Kaneto et al., "Expression of heparin-binding epidermal growth factor-like growth factor during pancreas development; A potential role of PDX-1 in transcriptional activation," *J Biol Chem*, 272:29137-29143 (1997).

J.F. Habener et al., "A newly discovered role of transcription factors involved in pancreas developmentand the pathogenesis of diabetes mellitus," *Proc Assoc Am Phys*, 110:12-21 (1998).

L. Bouwens, "Transdifferentiation versus stem cell hypothesis for the regeneration of islet beta-cells in the pancrease," *Microscopy Research & Technique*, 43:332-336 (1998).

J.C. Jonas et al., "Chronic hyperglycemia triggers loss of pancreatic beta cell differentiation in an animal model of diabetes," *J Biol Chem*, 274:14112-14121 (1999).

D.T. Finegood et al., "Prior streptozotocin treatment does not inhibit pancreas regeneration after 90% pancreatectomy in rats," *Am J Physiol*, 276:E822-E827 (1999).

R.N. Wang et al., "Beta-cell growth in adolescent and adult rats treated with streptozotocin during the neonatal period," *Diabetologia*, 39:548-557 (1996).

A. Pick et al., "Role of apoptosis in failure of beta-cell mass compensation for insulin resistance and beta-cell defects in the male Zucker diabetic fatty rat," *Diabetes*, 47(3):358-64 (1998).

V.K. Ramiya et al., "Reversal of insulin-dependent diabetes using islets generated in vitro from pancreatic stem cells," *Nature Medicine*, 6(3):278-282 (2000).

S. Bonner-Weir et al., "In vitro cultivation of human islets from expanded ductal tissue," *Proc. Natl. Aca. Sci USA*, 97(14):7999-8004.

Hui, Hongxiang et al., "Transfection of Pancreatic-Derived Beta-Cells with a Minigene Encoding for Human Glucagon-Like Peptide-1 Regulates Glucose-Dependent Insulin Synthesis and Secretion," *Endocrinology*, vol. 143, No. 9, pp. 3529-3539 (Sep. 2002).

Perfetti, R. et al., "Gene Therapy of Pancreatic-Derived Beta Cells with GLP-1 Restores Glucose-Dependent Insulin Production," *Diabetologia*, vol. 44, No. supplement 1, p. A-121 (Aug. 2001).

Perfetti, R. et al., "Transfection with GLP-1 to Produce Glucose-Dependent Insulin-Secreting Cells," *Cell Transplantation*, vol. 10, No. 6, pp. 515-516 (2001).

Chepurny, O.G., et al., "Over-expression of the glucagon-like peptide-1 receptor on INS-1 cells confers autocrine stimulation of insulin gene promoter activity: a stragegy for production of pancreatic beta-cell lines for use in transplantation," *Cell and Tissue Research*, vol. 307, No. 2, pp. 191-201 (Feb. 2002).

Orskov, C. et al., "Complete Sequences of Glucagon-like Peptide-1 from Human and Pig Small Intesting," *Journal of Biological Chemistry*, vol. 264, No. 22, pp. 12826-12829 (Aug. 1989).

Database Swissprot Online, Database accession No. P01274 (Nov. 1, 1990).

\* cited by examiner

SEQUENCE LISTING

<160> NUMBER OF SEQ ID NOS: 9

<210> SEQ ID NO 1
<211> LENGTH: 37
<212> TYPE: PRT
<213> ORGANISM: Homo sapiens

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 39
<212> TYPE: PRT
<213> ORGANISM: Homo sapiens

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 31
<212> TYPE: PRT
<213> ORGANISM: Homo sapiens

<400> SEQUENCE: 5

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 6
<211> LENGTH: 228
<212> TYPE: DNA
<213> ORGANISM: Homo sapiens

<400> SEQUENCE: 6
tggttgatga acaccaagag gaaccggaac aacattgcca acgtcatga tgaatttgag      60 aggcatgctg aagggacctt taccagtgat gtgagttctt acttggaggg ccaggcagca    120
aaggaattca ttgcttggct ggtgaaaggc cgaggaaggc gagacttccc ggaagaagtc    180
gccatagctg aggaacttgg gcgcagacat gctgatggat ccttctct                 228

<210> SEQ ID NO 7
<211> LENGTH: 28

```
<212> TYPE: DNA
<213> ORGANISM: Unknown
<220> FEATURE:
<223> OTHER INFORMATION: PCR Primer

<400> SEQUENCE: 7
acaagcttgg ttgatgaaca ccaagagg                                              28

<210> SEQ ID NO 8
<211> LENGTH: 28
<212> TYPE: DNA
<213> ORGANISM: Unknown
<220> FEATURE:
<223> OTHER INFORMATION: PCR Primer

<400> SEQUENCE: 8
cgctgcagag agaaggatcc atcagcat                                              28

<210> SEQ ID NO 9
<211> LENGTH: 19
<212> TYPE: DNA
<213> ORGANISM: Rat

<400> SEQUENCE: 9
agagccctta atggccaaa                                                        19
```

GLUCOSE-DEPENDENT INSULIN-SECRETING CELLS TRANSFECTED WITH A NUCLEOTIDE SEQUENCE ENCODING GLP-1

FIELD OF THE INVENTION

Embodiments of the present invention are directed to insulin-secreting cells transfected with a nucleotide sequence encoding for glucagon-like peptide-1 (GLP-1). The sequence is associated with an appropriate promoter. Cells prior to transfection secrete insulin constitutively and are insensitive to glucose (that is, they secrete the same amount of insulin all the time); cells after transfection secrete insulin in an amount that depends on the glucose they are exposed to (that is, they secrete the appropriate amount of insulin at the right time).

BACKGROUND OF THE INVENTION

Insulin is essential for proper metabolism in humans: in addition to its familiar role as the chief regulator of blood sugar levels in humans, it is essential for carbohydrate, lipid, and protein metabolism, as well. Pancreatic beta (β) cells of the islets of Langerhans, epithelial cells dispersed throughout the pancreas, secrete insulin. When β cells are destroyed or their function impaired, insulin production declines, and diabetes results.

Diabetes currently affects about 14 to 16 million individuals in the United States alone. Diabetes is a chronic condition characterized by an abnormally elevated plasma glucose level. The condition may result from an absolute deficiency of insulin due to the autoimmune destruction of insulin-secreting cells (i.e., Type I diabetes), or it may result from a relative deficiency of insulin due to either a secretory defect of production (i.e., by insulin-synthesizing cells) and/or by a resistance to the action of insulin (i.e., Type II diabetes).

For those patients that respond to insulin therapy, limitations remain in the methods of administering the hormone. For instance, insulin may be administered to a diabetic patient by way of an insulin pump. However, conventional insulin pumps deliver insulin to a patient at a set, constant rate (e.g., by pre-determined bolus size). Thus, the patient must constantly monitor his own blood glucose levels, by taking blood samples four or five times each day. Careful blood glucose monitoring is essential, since there is an ongoing risk of administering too much insulin, which may cause hypoglycemic shock. Hypoglycemic shock may cause a coma, and, not infrequently, may be fatal.

Drugs that promote insulin secretion or that lower glucose levels by other means are commonly prescribed to treat patients with type II diabetes. Sulfonylureas are the principal drugs prescribed to such patients. They stimulate insulin production by directly stimulating β cells; the effectiveness of such drugs therefore depends on the number of functioning β cells remaining in the pancreas. Repaglinide also stimulates insulin production by stimulating β cells, but differs structurally from the sulfonyluereas. Other drugs, such as metformin and troglitazone (known better by its brand name, REZULIN®), lower glucose levels by reducing glucose production in the liver and by promoting insulin sensitivity. Another drug, acarbose, inhibits digestive enzyme secretion and thereby delays digestion of carbohydrates (which when broken down in the body ultimately yield glucose). The efficacy of these drugs is tested first in vitro using existing cell lines that seek to model insulin-secreting β cells. None of these cell lines provides a satisfactory model, however, because they lose their responsiveness to glucose. As a result, in vitro studies of insulin-secreting drugs currently provides only limited information regarding their efficacy.

Understanding the function and development of insulin-secreting β cells is a critical step in developing better drugs to treat—and ultimately cure—diabetes. Pancreatic endocrine and exocrine cells (the cells that secrete insulin and other hormones) originate from a precursor epithelial cell during the development of the pancreas. G. Teitelman and J. K. Lee, "Cell lineage analysis of pancreatic islet cell development: glucagon and insulin cells arise from catecholarninergic precursor present in the pancreatic duct." *Dev. Biol.* 121:454–466 (1987); R. L. Pictet et al., "An ultrastructual analysis of the developing embryonic pancreas." *Dev. Biol.* 29:436–467 (1972) (the foregoing publications, and all other publications cited herein, are incorporated by reference in their entirety). Various differentiation factors are required to achieve the mature phenotype characteristic of islet β cells.

New β cells are formed from existing islets and from ductal epithelial cells. The latter source has greater intrinsic biological relevance. Indeed, the possibility of differentiating insulin-secreting cells from non-endocrine cells supports the hypothesis that the biological source (pancreatic ductal epithelium) for this compensatory mechanism may be present even in the setting of a generalized destruction of the entire population of islet β cells. This is strongly supported by recent studies demonstrating that primary cultures of epithelial ductal cells (from human and mouse pancreas) are susceptible to undergo differentiation into endocrine cells. V. K. Ramiya et al., "Reversal of insulin-dependent diabetes using islets generated in vitro from pancreatic stem cells." *Nature Medicine*, 6(3):278–82 (2000); S. Bonner-Weir et al., "In vitro cultivation of human islets from expanded ductal tissue. *Proc. Nratl. Aca. Sci. USA*, 14:7999–8004 (1997).

An incretin hormone, glucagon-like-peptide-1 (GLP-1), is believed to play a role in the development of the pancreas, though researchers have disagreed as to precisely what this role is. A decade ago, for example, U.S. Pat. No. 5,120,712, the entirety of which is incorporated by reference, stated that "The failure to identify any physiological role for GLP-1 caused some investigators to question whether GLP-1 was in fact a hormone and whether the relatedness between glucagon and GLP-1 might be artifactual." Researchers have more recently learned that GLP-1 has a function in rats. Bonner-Weir et al., for example, demonstrated that an analog of the incretin hormone glucagon-like-peptide-1 (GLP-1), termed exendin-4, was able to increase islet mass in adult animals previously subjected to subtotal pancreatectomy. G. Xu et al., "Exendin-4 stimulates both beta-cell replication and neogenesis, resulting in increased beta-cell mass and improved glucose tolerance in diabetic rats." *Diabetes* 48:2270–2276 (1999). Similarly, one of the inventors has demonstrated that treating glucose-intolerant aging Wistar rats with GLP-1 restored normal glucose tolerance and induced islet cell proliferation. Y. Wang et al., "Glucagon-like peptide-1 can reverse the age-related decline in glucose tolerance in rats." *J Clin Invest* 99:2883–2889 (1997).

Islet duodenal homeobox-1 ("IDX-1," also known variously as IPF-1/STF-1 and PDX-1) is a homeodomain protein and an insulin gene transcription factor expressed in the early pancreatic gland of the embryo. During pancreatic islet development, IDX-1 plays an important role in determining islet cell differentiation. It is the early IDX-1 gene expression during embryogenesis, coupled with the activation of other transcription factors (for example, NeuroDBeta 2, Pax 4, etc.), that determine the pancreatic endocrine hormone production. In adult (mature) animals, the expression of IDX-1 is repressed in the majority of pancreatic cells, with the exception of the β- and δ-cells (somatostatin-secreting cells) of the islets of Langerhans.

The mechanisms regulating proliferation and differentiation of the pancreatic hormone-producing cells and the chronology of these biological events are still largely undetermined. The sequence of events one of the inventors describes in U.S. patent application Ser. No. 09/920,868, filed Aug. 2, 2001, now U.S. Pat. No. 6,642,003, issued Nov. 4, 2003, suggests that the ability of regulating glucose uptake by the islet-specific glucose transporter GLUT2 is the first step necessary for the "sensitization" of the regulatory region(s) of the insulin gene to glucose. This would then promote the transcription of insulin mRNA. GLP-1-dependent activation of IDX-1 would further "commit" these cells toward a β cell-like pathway of differentiation by inducing the synthesis of glucokinase, the chief element of the "glucose-sensing machine" of the islets of Langerhans.

Researchers have learned much of the role of GLP-1 and IDX-1 in the rat and mouse, where knock-out mouse or other animal models were available to study the role of these hormones. Researchers know little of the role GLP-1 and IDX-1 in the development of human insulin-secreting cells, or of their interaction with other hormones present in the endocrine system. There is therefore an important need in the art for an analytical tool that permits researchers to elucidate the role of GLP-1 and IDX-1 in humans. A human model would be of immense importance in testing theories of endocrine development, in evaluating antidiabetic drugs, and developing new approaches to treat diabetes.

An important need exists in the art to implement the insulin-regulating abilities of GLP-1. Numerous disease conditions are related to the failed or deteriorated insulin regulation properties of particular cells in the body, such as diabetes; or the substantial lack of these cells in the body. Technology incorporating the insulin-regulating abilities of GLP-1 may obviate these disease conditions. A variety of potential insulin delivery applications may similarly be implemented in conjunction with this technology, such as insulin pumps which reside exterior to the body and implantable structures that release insulin internally in a glucose-dependent fashion.

SUMMARY OF THE INVENTION

It is an object of the present invention to provide a method for administering insulin to a human or animal in a dose-dependent response to glucose levels. Insulin may be administered in a glucose dose-dependent fashion via a device including the insulin-secreting cells of the present invention that resides exterior to the body, yet is in communication with an interior body fluid. Alternatively, a device including the insulin-secreting cells of the present invention may be implanted within the body, and similarly produce insulin in a glucose dose-dependent fashion.

It is a further object of the present invention to provide a method for treating a disease condition that results from the failed or deteriorated insulin regulation properties of particular body cells, or a substantial lack of these cells. Diabetes is one example of such a disease condition.

It is still a further object of the present invention to provide a model and analytic tool to study human insulin-secreting cells. Such an analytic tool may be used to investigate the function and development of pancreatic cells. It is yet a further object of the present invention to provide a human model that permits one to test theories of endocrine development, to evaluate drugs that stimulate insulin secretion, and to develop new approaches to treat diabetes.

Disclosed herein are insulin-secreting cells transfected with a minigene that encodes GLP-1, the minigene preferably including a suitable promoter operably associated with the nucleotide sequence encoding GLP-1. The transfected, insulin-secreting cells surprisingly secrete insulin in a dose-dependent manner; that is, the more glucose these cells are exposed to, the more insulin they secrete. This important feature regarding the transfected cells make them both a suitable model to test antidiabetic drugs, such as sulfonylureas, repaglinide, and other drugs, that are commonly administered to patients with type II diabetes, as well as a potential basis for dose-dependent, insulin-secreting mechanisms of treating diabetes, and similar disease conditions.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIGS. 1A and 1B are representations of two plasmid constructs (A: CMV/GLP-1 and B: RIP/GLP-1) generated with a human GLP-1 minigene. FIG. 1C is a representation of an area of a human proglucagon gene utilized to generate a GLP-1 insert.

FIG. 2A depicts cells transfected with a plasmid containing human GLP-1 driven by the CMV promoter (Lane 1); parental MIN-6 cells (Lane 2); and MIN-6 cells transfected with the vector alone (Lane 3). FIG. 2B depicts cells transfected with a plasmid containing human GLP-1 driven by the rat insulin promoter (Lane 4), and parental MIN-6 cells (Lane 5). Each experiment was repeated twice, using RNA samples from independent cultures.

FIGS. 3A–C represent one individual experiment, while FIGS. 3D–F are the graphical average of at least three independent northern blot analyses. FIGS. 3A and 3D: parental MIN-6 cells; Panels 3B and 3E: MIN-6 CMV/GLP-1 cells; and FIGS. 3C and 3F: MIN-6 RIP/GLP-1 cells. Insulin and GLP-1 mRNA levels were normalized by β-actin mRNA levels for each individual blot. Statistical significance of the data was evaluated by ANOVA.

FIGS. 7A, 7B, and 7C represent parental MIN-6 cells cultured in glucose-free medium (A), 6 mM glucose (B), and 12 mM glucose (C), respectively. FIGS. 7D, 7E, and 7F represent CMV/GLP-1 MIN-6 cells cultured in glucose-free medium (D), 6 mM glucose (E), and 12 mM glucose (F), respectively. FIGS. 7G, 7H and 7I represent RIP/GLP-1 MIN-6 cells cultured in glucose-free medium (G), 6 mM glucose (H), and 12 mM glucose (I), respectively.

FIG. 8A depicts an individual western blot analysis, and FIG. 8B graphically depicts the average of three independent experiments, with the GLP-1 receptor levels normalized by the total protein content of each individual cell extract.

FIG. 9A: Lane 1 indicates incubation of the radiolabeled A1 oligonucleotide sequence in the absence of nuclear extracts; Lane 2 indicates nuclear extracts incubated in the presence of a 100× non-labeled A1 oligonucleotide sequence, and a labeled element (cells were cultured in the presence of 10 mM glucose); Lane 3 through Lane 7 indicate nuclear extracts of cells cultured in the presence of 0 mM, 3 mM, 6 mM, 10 mM and 15 mM glucose, respectively; Lane 8 indicates incubation of nuclear extracts of cells cultured with 15 mM glucose in the presence of an IDX-1 antibody. FIG. 9B depicts the binding of nuclear proteins to the A1 element of the insulin promoter from RIP/GLP-1 MINE cells cultured in the presence of different concentrations of glucose. The bar graph represents the average of three independent experiments and is expressed in arbitrary units with the binding to cells cultured in the absence of glucose considered equal to 1. Statistical significance of the data was evaluated by Student's t test.

FIG. 10A depicts cAMP levels normalized for protein content. FIG. 10B depicts the amount of insulin released into the culture medium. FIG. 10C depicts mRNA levels for insulin and β-actin. The blot in FIG. 10C indicates one individual experiment. Repetition of the experiment using RNA extracts from independent cultures produced very similar results. Statistical significance of the data for mRNA and protein levels were evaluated by unpaired Student's t test.

DETAILED DESCRIPTION OF THE INVENTION

Figure 1:
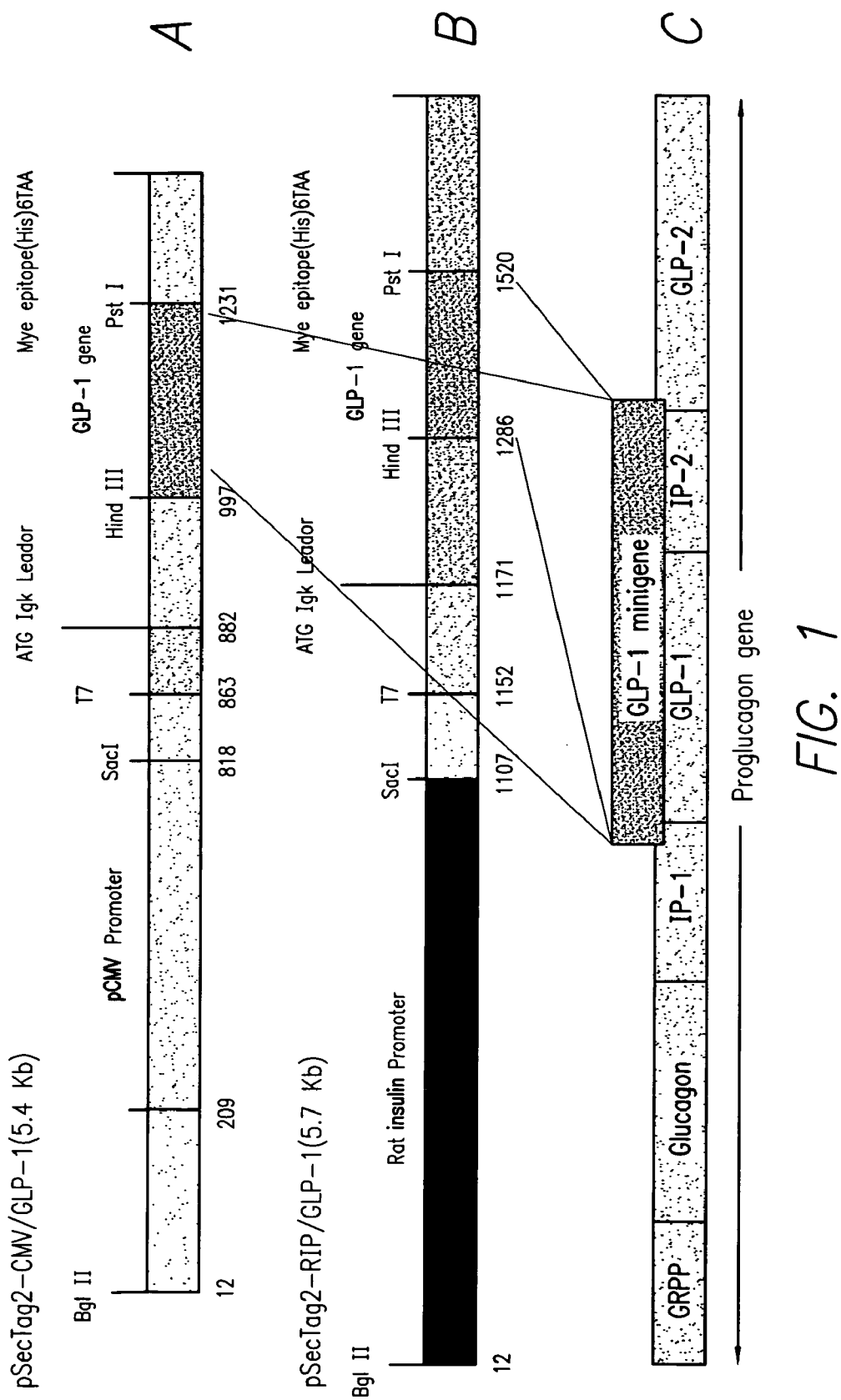
FIGS. 1A–C are schematic representations of plasmid constructs.

The present invention is based on the inventors'discovery that gene transfection with a minigene encoding for human GLP-1 and including a suitable promoter imparts to insulin-secreting cells the capability to synthesize insulin in a dose-dependent response to glucose levels.

The method of the invention comprises the steps of providing insulin-secreting cells, and transfecting the cells with DNA or mRNA that leads to the expression of GLP-1 or an analog of GLP-1, the DNA or mRNA preferably being operatively associated with a suitable promoter.

The inventors believe that active GLP-1 derives from a precursor protein composed of 37 amino acids (SEQ ID NO. 1) that, in order to be capable of inducing the secretion of insulin, needs to be cleaved of its first six amino acids. The 7–37 length of amino acids constitutes the active form of GLP-1 (SEQ ID NO. 2), and is the form of GLP-1 most preferred for use in accordance with the present invention. This active form is rapidly transformed to an inactive state when it loses two additional amino acids to become 9–36 GLP (SEQ ID NO. 3). In a preferred embodiment of the present invention, cells may be transfected with the precursor protein, as described in the ensuing Examples, thereby generating the active form of GLP-1 upon the cleavage of the first six amino acids.

A variety of GLP-1 analogs may be used in accordance with the present invention. These analogs may include, but are not limited to, precursor protein to GLP-1, inactive GLP-1, Exendin-4 (SEQ ID NO. 4; an agonist of the GLP-1 receptor), or Exendin-9 (SEQ ID NO. 5; an antagonist of the GLP-1 receptor).

Any β cell or insulin-secreting cell may be used in the methods of the present invention, including, but not limited to, cells of the islet of Langerhans (such as A, B, D, and F islet cells), epithelial cells of intralobular ducts, acinar cells, centroacinar cells, basket cells, or any other pancreatic exocrine cells—whether they secrete insulin or digestive enzymes—and their associated ducts. Any cell line of insulin-secreting or pancreatic cells may be used in accordance with the present invention, including, for example, AsPc-1, AR42J, BxPc-3, Capan-1, Capan-1, Capan-2, Capan-2, Colo357, HPAC, HPAF, HPAF, HPAF-II, Hs766T, human insulinoma cell line, MiaPaCa, MIAPaCa-2, PANC-1, Panc-1, Panc89, QGP-1, S2CP9, T3M4, or any other pancreatic cell line whether derived from human, rat, or other animal.

In a preferred embodiment, an insulin-secreting cell is transfected with a DNA fragment of the human proglucagon gene containing the nucleotide sequence encoding for human GLP-1 (the DNA fragment is shown at FIG. 1C and identified by SEQ ID NO. 6). LIPOTAXI® (available from Stratagene of La Jolla, Calif.) is preferably used as the transfection reagent. The DNA fragment preferably contains the coding region for human GLP-1, a partial fragment of an IP sequence at the 5'-end, and a fragment of a GLP-2 sequence at the 3'-end. The fragments of the IP and GLP-2 sequences may be of varying lengths, but preferably include nucleotides 289 to 516 of human proglucagon cDNA.

In alternative embodiments, one may use other methods of transfecting cells, such as coprecipitation of DNA with calcium phosphate ($CaPO_4$); "lipofection" with cationic liposomes; transfection with polyethylenimine; transfection by electroporation, in which a single pulse of high-current electricity is applied to a preparation of DNA and cells; receptor-mediated endocytosis; or any other method known to transfer genetic material into cells. The transfection method employed depends on the pancreatic cell used, and should be readily apparent to one of ordinary skill in the art of molecular biology.

As depicted in FIG. 1, the nucleotide sequence contained in the insulin-secreting cells of the present invention may be operatively associated with a promoter. Any suitable promoter may be used in accordance with the present invention, such as human promoters that have a glucose-responsive element or insulin promoters of other animal species. Appropriate promoters may include, but are not limited to, rat insulin II promoter (RIP) and rat insulin 7 promoter. It will be readily appreciated by one of skill in the art that the human promoter is substantially longer than RIP and rat insulin 7 promoter, but no undue experimentation is required to utilize such a human promoter in accordance with the various embodiments of the present invention.

After transfecting cells, one may select cells that are successfully transfected from cells that are not. A preferred method of selecting cells is by transfecting, along with genetic material that encodes GLP-1, genes that confer resistance to drugs that disrupt the cells' growth. A list of gene/drug combinations that may be used to select cells in this manner is set forth below in Table 1:

TABLE 1

Gene/drug combinations that may be used to select cells successfully transfected with genetic material that encodes GLP-1

| RESISTANCE GENE | DRUG |
| --- | --- |
| Aminoglycoside phosphotransferase (AGPT; neo$^r$) | Neomycin geneticin sulfate |

TABLE 1-continued

Gene/drug combinations that may be used to select cells successfully transfected with genetic material that encodes GLP-1

| RESISTANCE GENE | DRUG |
| --- | --- |
| Hygromycin phosphotransferase (hyg$^r$) | Hygromycin B |
| Puromycin N-acetyl transferase (puro$^r$) | Puromycin |
| Histidinol dehydrogenase (S. typhimurium hisD) | Histidinol |
| Dihydrofolate reductase (DHER) | Methotrexate |

An especially preferred method of selecting cells is by culturing cells transfected with AGPT in the presence of G418 sulfate (available as "GN-04" from Omega of Tarzana, Calif.). A preferred concentration of G418 sulfate is 400 µg/ml.

The cells of the present invention may be used to investigate the development and function of the pancreas, the cells that constitute it, and the secretions it produces. They may also be used to investigate the efficacy of drugs that promote insulin secretion. As previously discussed, such drugs are commonly administered to patients with type II diabetes, who often display a resistance to insulin. These drugs include sulfonylureas, repaglinide, metformin, troglitazone, and others. One could test these drugs according to the usual protocol: obtain cells according to the present invention; expose the drug to be tested to the cells; and measure the insulin secreted.

The cells of the present invention may further be used in the treatment of diseases or conditions wherein it may be advantageous to provide cells that secrete insulin in a dose-dependant fashion based upon glucose levels either locally or systemically. The cells may be included in an apparatus that administers insulin to a human or animal; the apparatus being either implanted within or residing exterior to the body. Such an apparatus may receive interstitial fluid, blood, or another body fluid and secrete insulin in a dose-dependent fashion in response to glucose levels in the interstitial fluid, blood, or other body fluid. In this manner, the apparatus may act as a biological insulin pump, useful in the treatment of, e.g., diabetes. One advantage of such an apparatus may be the elimination of the need for a patient to periodically check his blood glucose level by way of direct blood testing. This, and other features that provide an easier means for treating diabetes and similar disease conditions, may markedly improve an individual's quality of life.

In an exterior apparatus, the cells of the present invention may be included in a cartridge, or a similar, replaceable mechanism, such that the cells may be changed after a given time period (e.g., 2–3 weeks). Alternatively, a set of cells may be maintained in the exterior apparatus by regular introduction of appropriate nutrients and the like; thereby obviating the need to replace these cells. Moreover, the exterior apparatus may monitor a body glucose level by testing, for example, the interstitial fluid in the skin. This interstitial fluid may provide an indication of body glucose level, and the exterior apparatus may administer insulin to the body in a dose-dependent manner in response to this glucose level.

In an alternative embodiment, the cells of the present invention may be implanted into a human or other animal in an islet cell transplantation procedure. Islet cells may be harvested from a cadaver, engineered with GLP-1 to create the cells of the present invention, and implanted in a human or other animal.

Finally, a gene-therapy approach may be implemented in accordance with an embodiment of the instant invention. Indeed, a gene-transfer strategy may promote the incorporation of the GLP-1 minigene construct into cells of individuals without need of cell transplantation.

EXAMPLES

The Examples discussed herein demonstrate that insulin-secreting cells transfected with a nucleotide sequence encoding for human GLP-1 that is operably associated with a suitable promoter, such as RIP, are capable of synthesizing insulin in a dose-dependent response to ambient glucose levels. Absent the inclusion of the nucleotide sequence and promoter of the present invention, the insulin-secreting cells are insensitive to glucose, and secrete insulin constitutively (i.e., steady levels of secretion at all times).

Example 1

Creation of Cell Culture

Mouse insulinoma (MIN-6) cells were obtained from Dr. K. Silver (University of Maryland, Baltimore, Md.). Cells were cultured in DMEM medium (obtained from Gibco BRL; Gaithersburg, Md., hereinafter "Gibco") containing 100 µg/ml penicillin, 50 pg/ml streptomycin, and 10% fetal bovine serum ("FBS," obtained from Gemini Bio-Products, Inc.; Woodland, Calif.) at 37° C. under a humidified condition of 95% air and 5% $CO_2$. Gene and protein expression experiments were carried out using cells grown to 80% of confluence, after washing the cell layer with serum-free medium and a "wash-out" incubation for 2 to 12 hours with fresh medium.

To determine the response to various stimuli, cells were cultured in serum-free, glucose-free medium, and then exposed to medium containing increasing concentrations of glucose. At the completion of the experiments, media and cells were collected separately and assayed for the experiments described hereafter.

Example 2

Isolation of GLP-1 Minigene Construct

Human proglucagon was obtained from Dr. Daniel J. Drucker (University of Toronto; Toronto, Canada). Using a polymerase chain reaction (PCR), proglucagon cDNA was used to generate a DNA sequence spanning from nucleotide 289 to nucleotide 516 (SEQ ID NO. 6; FIG. 1). This PCR-generated sequence included the coding region for human GLP-1, a partial fragment of the IP sequence at the 5'-end, and a fragment of the GLP-2 sequence at the 3'end. The identity of the PCR product was confirmed by DNA sequencing.

Example 3

Plasmid Construction and Cell Transfection with Human GLP-1 Minigene

MIN-6 cells were transfected with a pSecTag2 A plasmid (obtained from Invitrogen; Carlsbad, Calif.) harboring the GLP-1 fragment of the human proglucagon gene using LIPOTAXI® (Mammalian Transfection Kit, Stratagene; La Jolla, Calif.). Two GLP-1 expressing vectors were generated (FIGS. 1A–B). In the first vector, the DNA fragment encoding for GLP-1 was inserted at the Hind-III and Pst-I sites of the pSecTag2 A plasmid, downstream of the cytomegalovirus (CMV) promoter. For the second expression vector, the CMV sequence was deleted by restriction enzyme digestion using the enzymes BgI-II and Sac-I and replaced with a DNA fragment encoding for the rat insulin-II promoter ("RIP," obtained from Dr. Theodore Friedman; King Drew Medical Center, Los Angeles, Calif.). The fragment of the RIP that was utilized corresponds to the RIP-7 promoter previously characterized in Shieh et al., "Cell-specific and ubiquitous factors are responsible for the enhancer activity of the rat insulin II gene," J. Biol. Chem. 266:16708–16714 (1991), and was inserted after digestion with BamH-1 and Hind-III restriction enzymes. Vector DNA and promoter sequence were blunted by incubation with the Klenow fragment prior to the ligation. The correct orientation of the sequence was verified by digesting the plasmid with EcoR-1.

Both constructs contained a signal peptide sequence on the 5'-end of the insert (FIG. 1). Control cells were transfected with the vector alone. The selection of positive (i.e., transfected) cells was carried out by culturing the cells in the presence of 400 µg/ml of G418 sulfate (obtained from Omega; Tarzana, Calif.).

Example 4

RNA Isolation and Northern Blot Analysis

Cellular RNA was extracted in accordance with conventional methods. Northern blots were hybridized with: (1) full-length rat insulin II cDNA probe; (2) human IDX-1 cDNA (obtained from Dr. Chris Wright; Vanderbilt University; Nashville, Tenn.); and (3) rat β-actin cDNA probe. The human GLP-1 cDNA probe was generated by PCR of the proglucagon plasmid utilized for cell transfection. The PCR product was generated using the primers set forth as SEQ ID NO. 7 and SEQ ID NO. 8.

Figure 2:
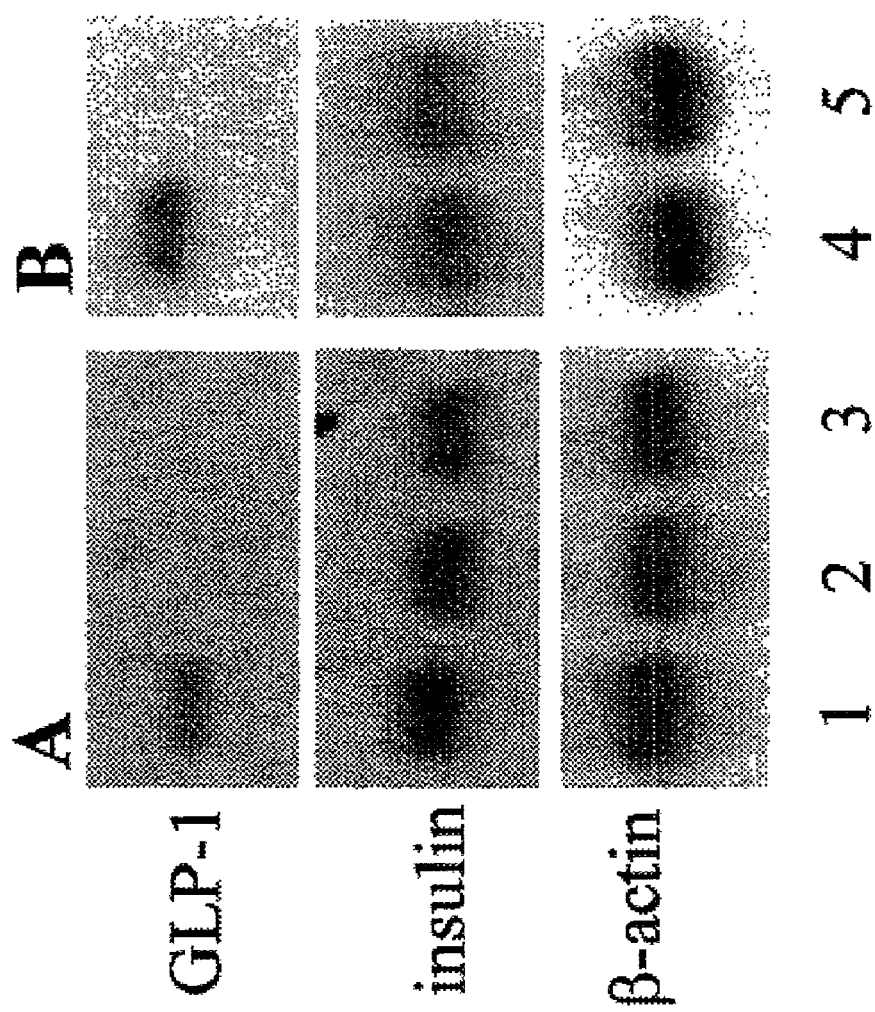
FIGS. 2A–B depict a northern blot analysis of control and GLP-1-transfected MIN-6 cells, respectively. Parental MIN-6 cells, MIN-6 cells transfected with the vector alone, or with a vector containing a DNA sequence encoding for human GLP-1 were cultured in 10% FBS, in the presence of 12 mM glucose. Cells were subjected to RNA extraction and northern blot analysis for GLP-1, insulin, and β-actin mRNA levels.

All cDNA probes were labeled with [$^{32}$P]dCTP (obtained from Amersham Life Science; Arlington Heights, Ill.) by the random priming procedure using the enzyme "sequenace" (obtained from United States Biochemical; Cleveland, Ohio). The mRNA level for individual transcripts was evaluated by densitometric analysis and normalized for the relative abundance of β-actin mRNA (FIG. 2).

Example 5

Immunofluorescence Microscopy

Cells were cultured on monocoated chamber slides (obtained from Nalge Nunc International; Naperville, Ill.) in the presence of different concentrations (e.g., 0 mM, 6 mM, and 12 mM) of glucose (obtained from Sigma Chemicals; St Louis, Mo., hereinafter "Sigma"), for 8 hours. Cells were washed and fixed with 2% paraformaldehyde for 4 hours, at room temperature in phosphate buffered saline (PBS; obtained from Gibco), solubilized with 0.1 % (vol/vol) Triton X-100 (obtained form Sigma) in PBS for 5 minutes. Cells were then washed with 0.01 M PBS three times for 3–5 minutes, and non-specific binding was inhibited by using 5% chick serum (obtained from Life Technologies, Inc.; Rockville, Md.) in 0.01 M PBS, at room temperature for 60 minutes in a humid chamber. A rabbit IDX-1 antibody (obtained from Dr. Chris Wright; Vanderbilt University) directed against the N-terminus of the frog homologue of the IDX-1 gene was used as the primary antibody (1:500 diluted with 0.1% Triton-X 100, 1% BSA in 0.01 M PBS), and slides were incubated at 4° C., overnight in a humid chamber. After washing, cells were incubated with a fluorescein-conjugated goat anti-rabbit IgG antibody (obtained from Molecular Probes, Inc.; Eugene, Oreg.) and incubated at room temperature for 1 hour in a humid chamber.

Figure 7:
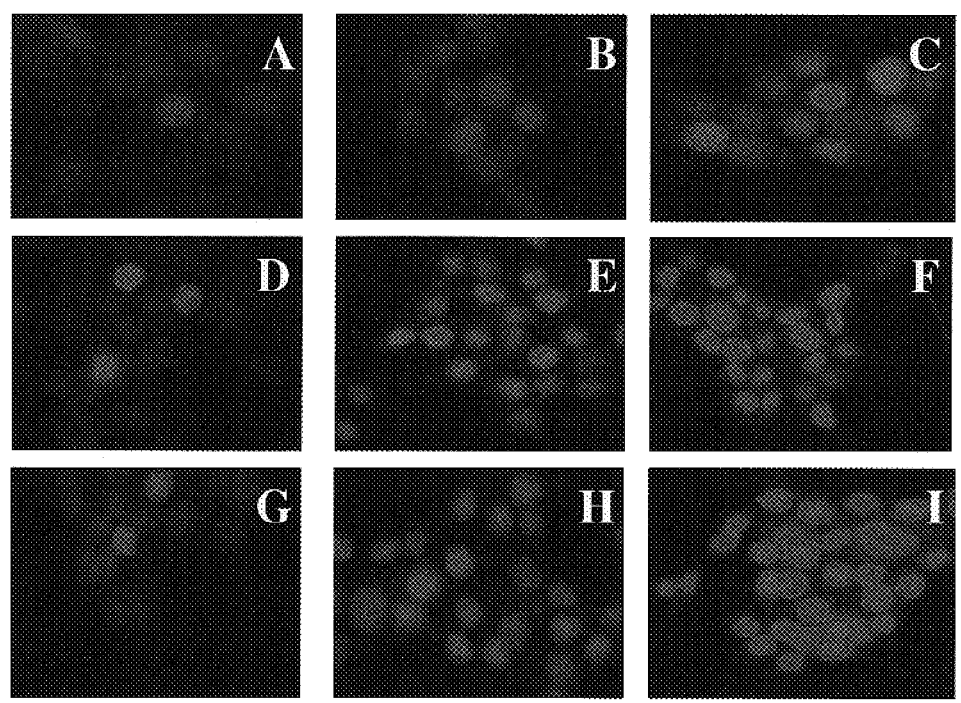
FIG. 7 is executed in color, and depicts the immunofluorocytochemistry for IDX-1 in cells exposed to various concentrations of glucose. CMV/GLP-1 cells, RIP/GLP-1 cells, as well as parental MIN-6 cells, were cultured in the presence of 6 mM glucose with 10% FBS. After a 2-hour wash-out incubation with glucose-free, serum-free medium, they were incubated with 0 mM, 6 mM or 12 mM glucose for 12 hours and subjected to immunostaining with an anti-IDX-1 antibody.

Immunofluorescence experiments were repeated at least three times using independent cell cultures (FIG. 7).

Example 6

Measurement of Insulin and GLP-1 Secretion

Figure 3:
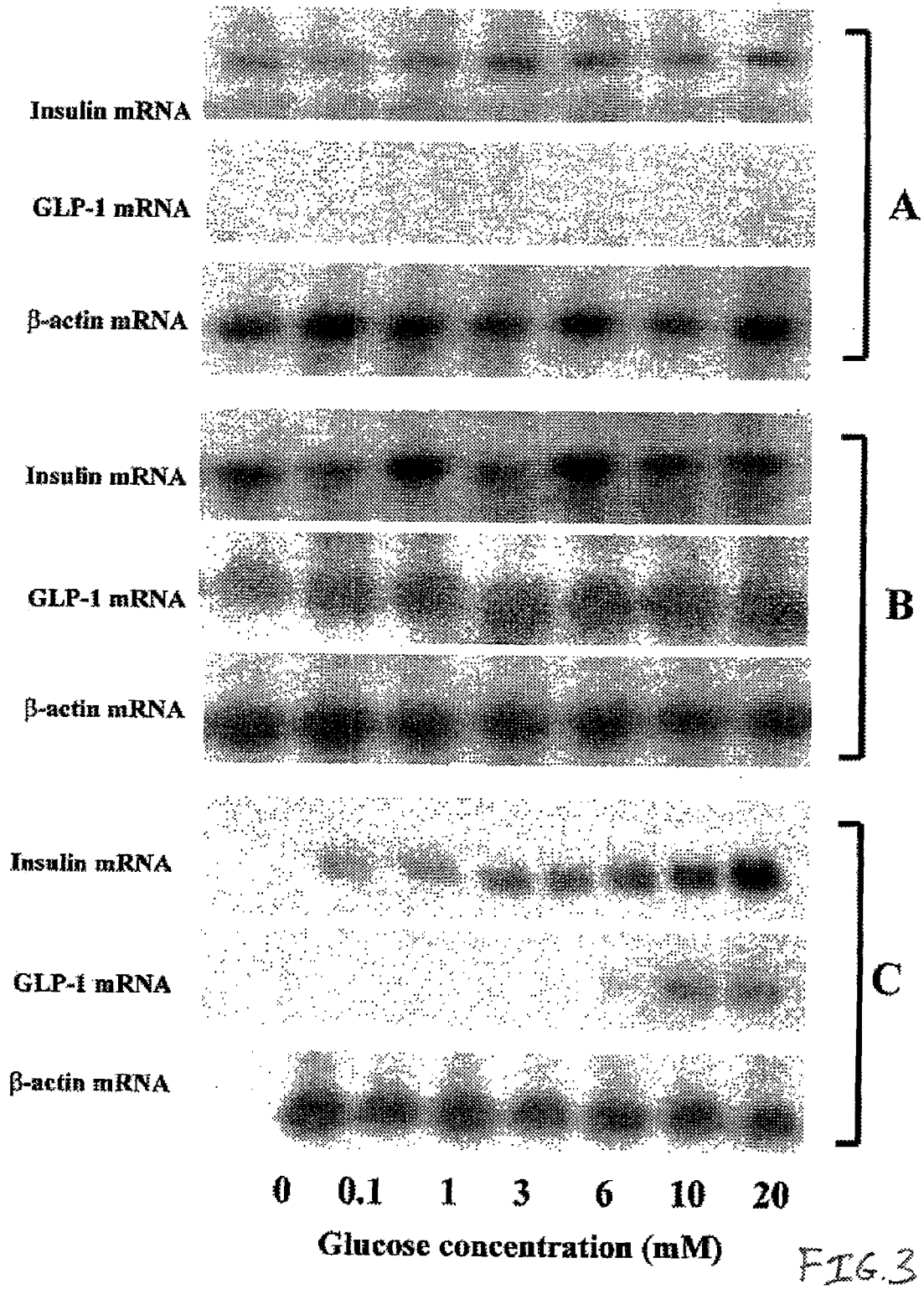
FIGS. 3A–F depict northern blot analysis for insulin and GLP-1 mRNAs. Cells routinely cultured in the presence of 10% FBS and 12 mM glucose were subjected to a 2-hour wash out period with medium deprived of glucose and FBS. They were then cultured in serum-free medium for 8 hours in the presence of various concentrations of glucose (e.g., 0 mM, 0.1 mM, 1 mM, 3 mM, 6 mM, 10 mM, and 20 mM). After RNA extraction, the membranes were hybridized with cDNA probes for insulin, GLP-1 and β-actin.
Figure 3:
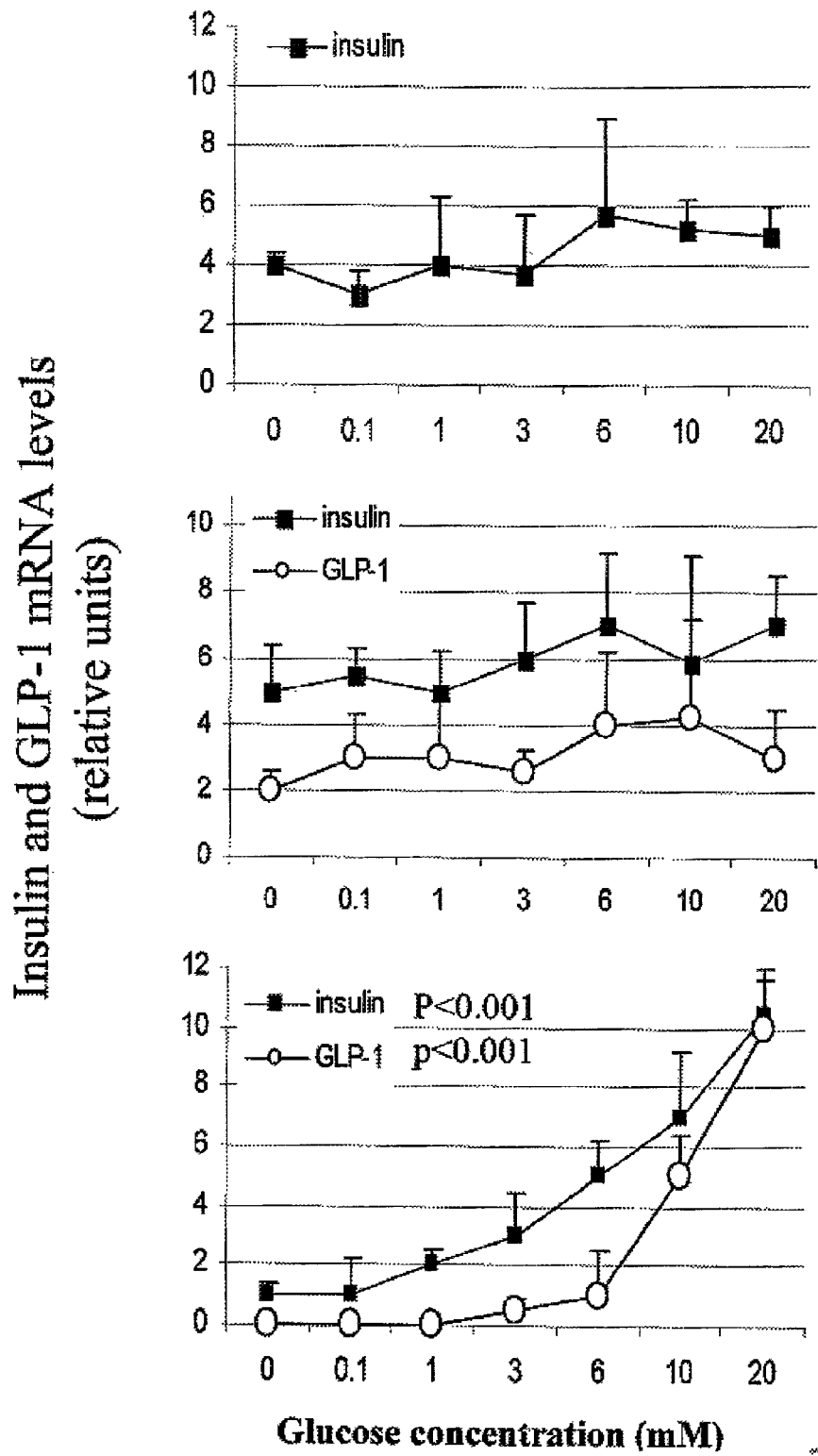

MIN-6 cells (parental; GLP-1/CMV-transfected; GLP-1/insulin promoter transfected; and transfected with the pSec-Tag2 A plasmid alone) were plated at density of $10^6$ cells/well in 6 well plates. Once the cells reached 80% of confluence, they were washed and exposed to fresh serum-free medium for 8 hours in the presence of various concentrations of glucose (e.g., 0 mM, 0.1 mM, 1 mM, 3 mM, 6 mM, 10 mM, and 20 mM). The level of insulin and GLP-1 in the culture medium was measured by radioimmunoassay (RIA kit, obtained from Linco Research Inc.; St. Charles, Mass.). Insulin and GLP-1 levels were then normalized for total cellular protein content per each individual culture (FIG. 3).

Figure 5:
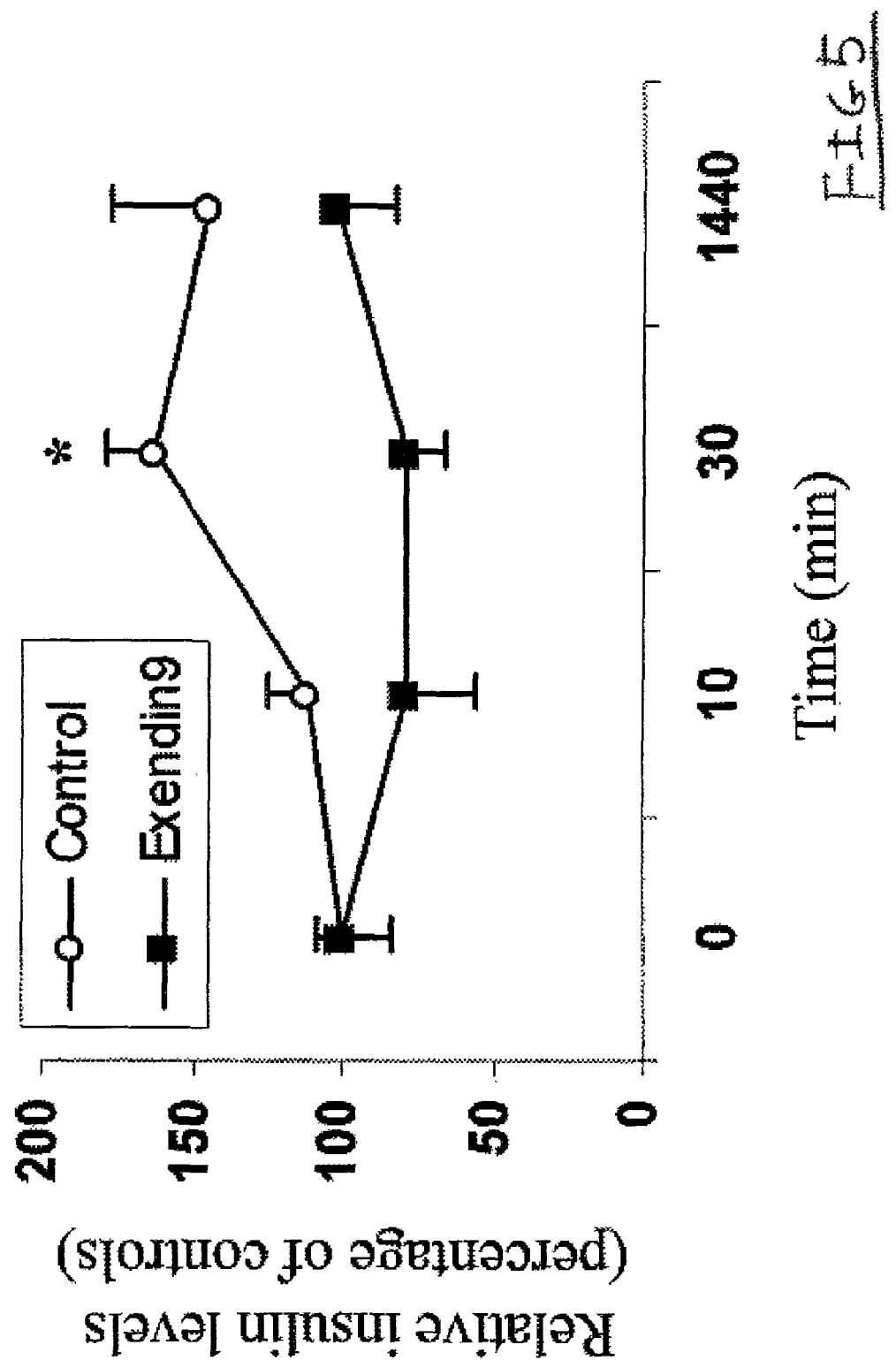
FIG. 5 graphically depicts inhibition of insulin secretion by the GLP-1 receptor antagonist Exendin-9. MIN-6 RIP/GLP-1 cells routinely cultured in the presence of 10% FBS and 12 mM glucose were subjected to an overnight wash out period with medium deprived of glucose and FBS. They were then cultured in serum-free medium in the presence of 10 mM glucose and Exendin-9 ($10^{-6}$ M) for increasing lengths of time. Insulin levels were normalized for protein content. Statistical significance of the data was evaluated by unpaired Student's t test.

To validate the specificity of GLP-dependent secretion of insulin, MIN-6 RIP/GLP-1 cells were cultured in the presence of the receptor antagonist Exendin-9 (obtained from American Peptide Company, Inc.; Sunnyvale, Calif.). After an overnight wash out period (in medium deprived of glucose and fetal bovine serum, FBS), cells were cultured in serum-free medium containing 10 mM glucose for various lengths of time (e.g., 10 minutes, 30 minutes, 1 hour, 24 hours), in the presence or absence of $10^{-6}$ M of Exendin-9. Conditioned media were then collected for RNA analysis for insulin level (FIG. 5).

Example 7

Protein Assay

Figure 6:
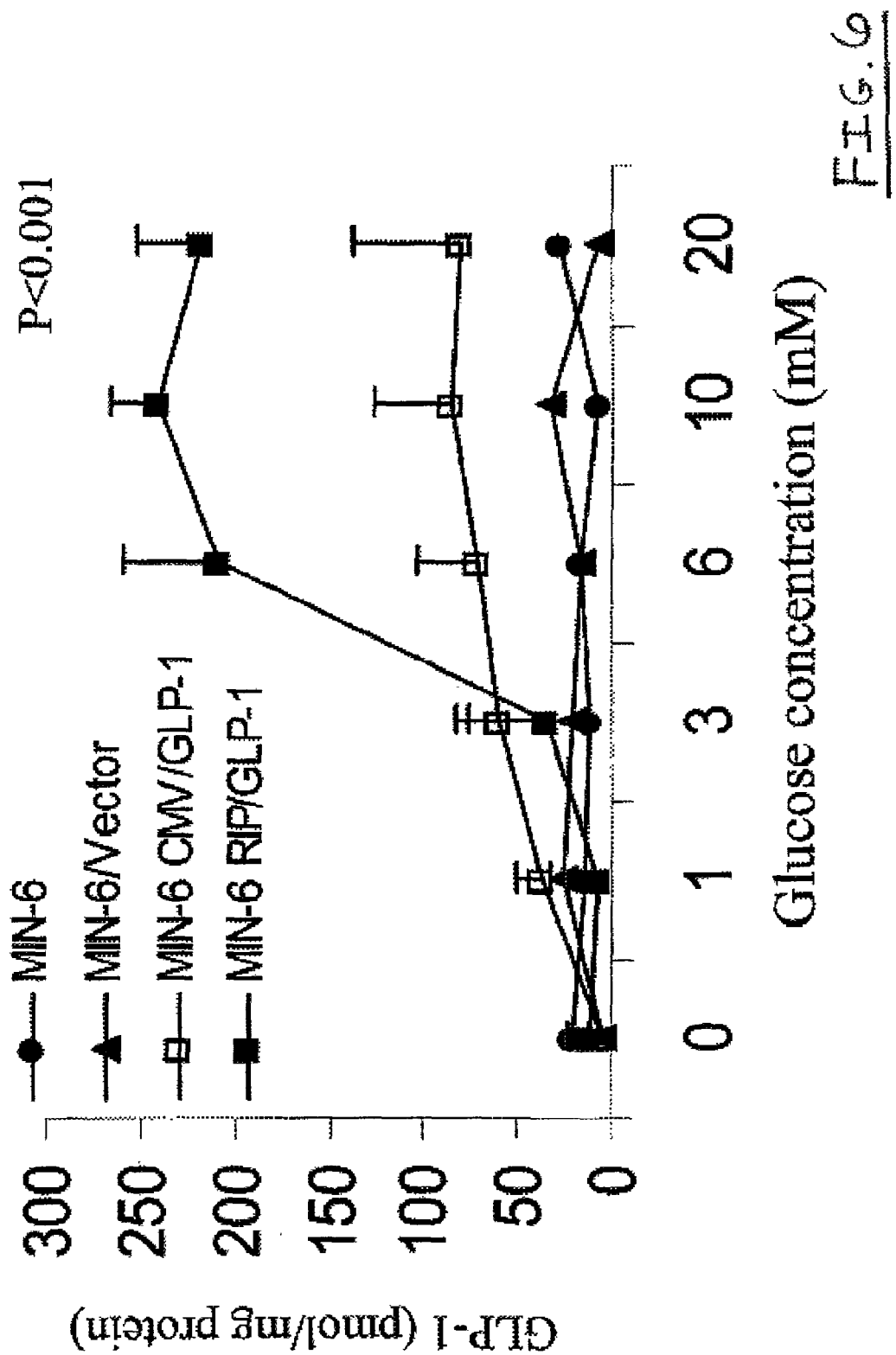
FIG. 6 graphically depicts glucose-dependent GLP-1 secretion in a culture medium. GLP-1 accumulation into the culture medium was determined after a 2-hour wash out period, carried out with serum-free and glucose-free medium. Parental MIN-6 cells, MIN-6 cells transfected with the vector alone, MIN-6 cells transfected with CMV/GLP-1, and MIN-6 cells transfected with RIP/GLP-1 were incubated in the presence of various concentrations of glucose for 8 hours. Each experiment was repeated at least four times and the data plotted on the graph represent the mean plus or minus one standard deviation. GLP-1 levels were normalized by the total protein level in each individual culture. Statistical significance of the data was evaluated by ANOVA.

Total cellular protein content was measured by utilizing the Bradford method (obtained from Bio-Rad; Richmond, Calif.). The quantity of proteins measured was used as a correction factor for the detection of the relative amount of insulin or GLP-1 in the culture medium, as assayed by RIA (FIG. 6).

Example 8

Protein Extraction and Western Blotting

MIN-6 cells were cultured in the presence of various concentrations of glucose (e.g., 0 mM, 3 mM, 6 mM, and 15 mM) for 8 hours and then washed, collected, and homogenized in ice-cold TE buffer (40 mM Tris, pH 7.4; 1 mM ethylenediamine tetra-acetic acid, EDTA; 1 mM dithoithreitol, DTT) (obtained from Sigma), in the presence of proteinase inhibitors (1 mM phenylmethylsufonyl fluoride; 8.3 μM aprotinin; 50 μM leupeptin; and 30 mM sodium orthovanadate) (obtained from Sigma), and spun at 90,000 g×min, for 30 minutes. Pellets were resuspended in TE buffer, supplemented with 0.3% w/v deoxycholate, and 1% w/v digitonin (obtained from Sigma), rotated at 4° C., and spun at 90,000×g for 30 minutes. Supernatants were collected. Cell homogenates were separated by sodium dodecyl sulfate polyacrylamide gel electrophoresis (SDS-PAGE) on a 4–12% polyacrylamide gel (obtained from Novex, San Diego, Calif.) and electroblotted onto a polyvinylidene fluoride (PVDF) membrane (obtained from Millipore; Bedford, Mass.).

Figure 8:
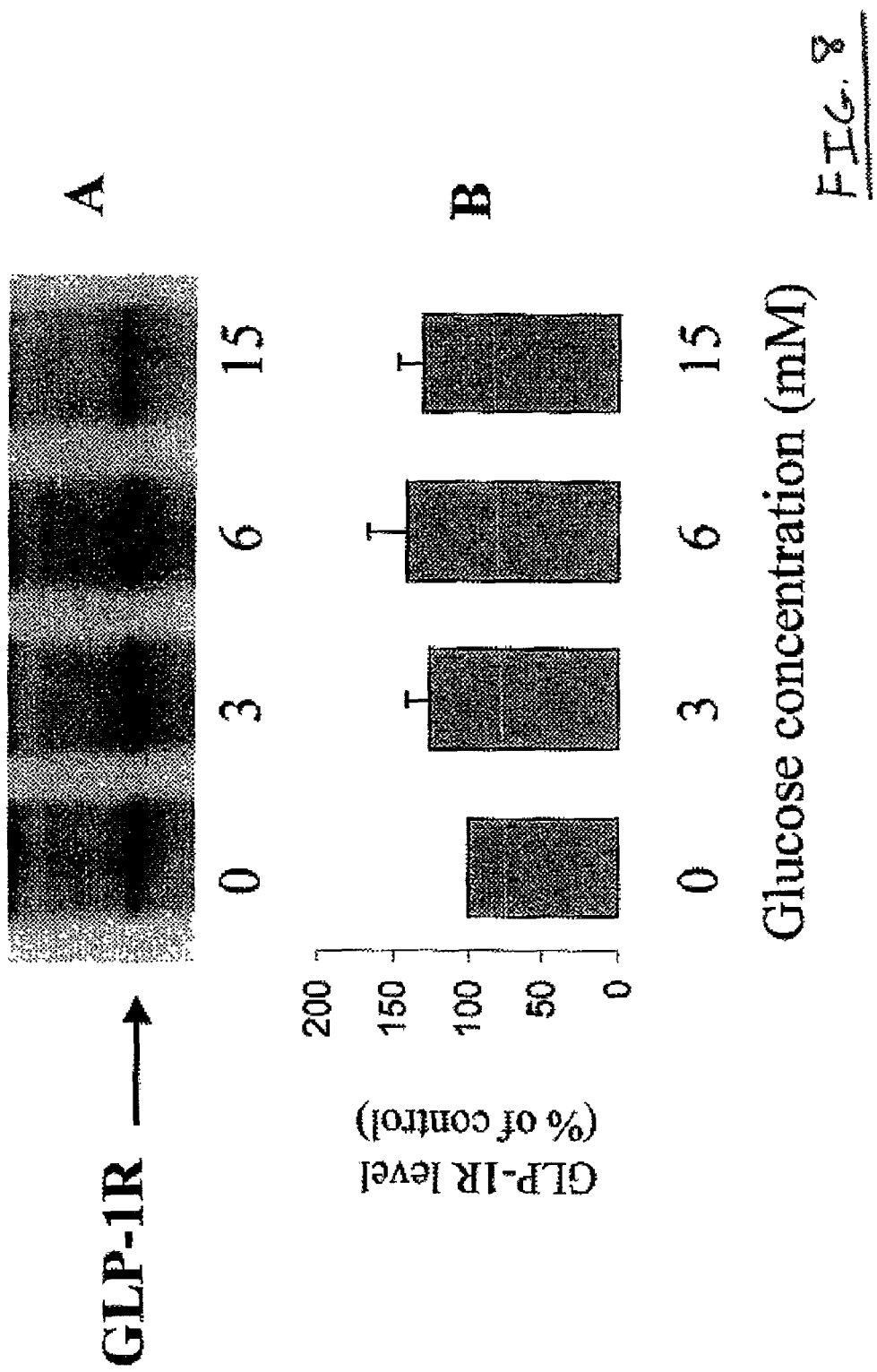
FIGS. 8A–B depict GLP-1 receptor expression in MIN-6 cells transfected with RIP/GLP-1. MIN-6 cells transfected with RIP/GLP-1 were cultured in serum-free medium in the presence of various concentrations of glucose (e.g., 0 mM, 3 mM, 6 mM, and 15 mM) for 48 hours. After removal of the culture medium, the cells were collected and the protein extract subjected to western blot analysis with a polyclonal antibody directed against human GLP-1 receptor.

The blot was then "blocked" in wash solution (PBS containing 3% milk and 0.1% Tween-20), probed with 1 μg/ml of a mouse anti human GLP-1 receptor (GLP-1R) antibody (obtained from Dr. D. Drucker) for 90 minutes at 25° C., washed twice with wash solution, incubated with anti-mouse secondary antibody for 1 hour at 25° C., and washed three times with wash solution. The protein band corresponding to the GLP-1R was visualized by the enhanced chemiluminescence (ECL) method (obtained from Amersham; Piscataway, N.J., hereinafter "Amersham") (FIG. 8).

Example 9

Gel Shift Analysis

For gel shift analysis (FIG. 9), an oligonucleotide corresponding to rat insulin-II A1 element (−89 to −69; SEQ ID NO. 9) was annealed and end-labeled using T4-polynucleotide kinase (obtained from Gibco) and γ-[$^{32}$P]ATP (obtained from Amersham). Nuclear extracts from RIP/GLP-1 MIN-6 cells cultured in the presence of various concentrations of glucose (e.g., 0 mM, 3 mM, and 10 mM) for 8 hours were prepared using the mini-extract method.

Gel shift reactions with nuclear proteins were carried out in 1 μg of poly DI-DC, 25 mM HEPES, 1.5 mM EDTA, 5% glycerol, 1.0 mM DTT, and 150 mM KCl in a final volume of 25 μl. The mixture of 10 μg of nuclear extracts and [$^{32}$P]-labeled DNA was incubated for 20 minutes at 25° C. For competition assays, an excess of specific or nonspecific competitor oligonucleotide was added (100-fold) 5 minutes before the addition of [$^{32}$P]-labeled DNA. Reaction mixtures were loaded onto a 4% polyacrylamide gel and subjected to electrophoresis at 90 V in 0.5×TBE [0.9 M Tris, 0.9 M borate, 2 mM EDTA (pH 8.0)]. Gels were dried and protein-DNA complexes were visualized by exposure to X-ray film for 4–12 hours. For supershift assays, before electrophoresis, gel shift reactions were incubated with 2 μg of IDX-1 antibody (obtained from Dr. Chris Wright) for 30 minutes on ice. Extracts were then subjected to electrophoresis and detected as described above.

Example 10

Inhibition of cAMP-Dependent GLP-1 Signaling

Figure 10:
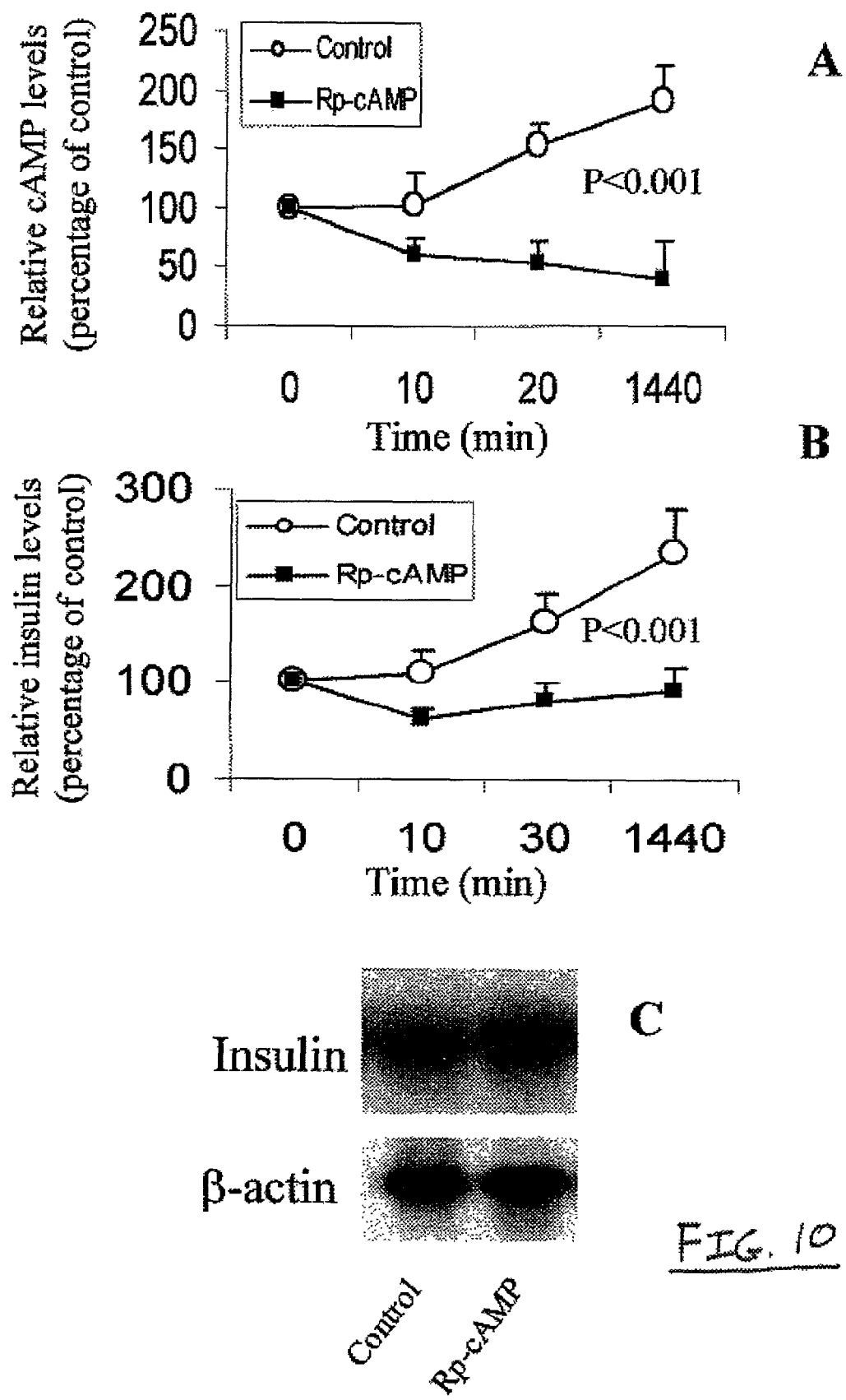
FIGS. 10A–C depict an effect of cAMP inhibition on glucose and GLP-1-dependent secretion of insulin and insulin mRNA levels. MIN-6 RIP/GLP-1 cells routinely cultured in the presence of 10% FBS and 12 mM glucose were subjected to an overnight wash out period with medium deprived of glucose and FBS. They were then cultured in serum-free medium in the presence of 10 mM glucose in the presence of Rp-cAMP ($10^{-6}$ M).

To investigate whether the ability of GLP-1-transfected cells to release insulin in a glucose-dependent fashion was dependent upon cAMP-dependent GLP-1 signaling, we tested the effect of the cAMP inhibitor RP-cAMP (which blocks the activation of protein kinase A, PKA, resulting from an elevation of cAMP) on insulin secretion and insulin mRNA levels (FIG. 10). MIN-6 RIP/GLP-1 cells routinely cultured in the presence of 10% FBS and 12 mM glucose were subjected to a overnight wash out period with medium deprived of glucose and FBS. They were then cultured with serum-free medium containing 10 mM glucose for various lengths of time (e.g., 10 minutes, 30 minutes, 1 hour, and 24 hours), in the presence or absence of $10^{-6}$ M of RP-cAMP (Adenosine-3', 5'-cyclic monophosphorothioate, Rp-isomer, Triethylammonium Salt), (obtained from Biosciences Inc.; La Jolla, Calif.).

Cells and conditioned media were collected for RNA analysis and for RIA of insulin and GLP-1 levels. Culture conditions, RNA extraction, RIA, and protein assay were performed as described in Examples above. Determination of cAMP levels was performed with a cAMP detection kit (obtained from Amersham), according to manufacturer's specifications.

Example 11

Statistical Analysis

The data were expressed as mean±S.E. Significance of the data was evaluated by unpaired Student's t test. One-way analysis of variance (ANOVA) was used to evaluate statistical significance when more than two data points were analyzed. Statistical analyses by unpaired Student's t test or ANOVA are discussed above.

Example 12

Northern Blot Analysis for Insulin and GLP-1 mRNAs

CMV/GLP-1 cells, RIP/GLP-1 cells, and cells transfected with the pSecTag2A plasmid alone, were cultured in the presence of increasing concentrations of glucose and subjected to northern blot analysis for detection of insulin, GLP-1, and β-actin mRNA levels. Northern blot analysis of MIN-6 cells transfected solely with the pSecTag2A showed that the insulin gene was constitutively transcribed and that the insulin mRNA level was not effected by varying the concentration of glucose in the culture medium (FIGS. 3A and 3D). Cellular transfection of MIN-6 cells with a plasmid harboring the CMV/GLP-1 construct did not restore the glucose-dependent transcription of the insulin gene characteristic of normal islet β-cells (FIGS. 3B and 3E).

Transfection with RIP/GLP-1 construct promoted a profoundly different profile in the glucose-dependent accumulation of insulin mRNA (FIGS. 3C and 3F). There was a sharp increase in the expression of insulin mRNA that paralleled the increase in the concentration of glucose in the culture medium ($p<0.001$). Detection of GLP-1 mRNA in the various cell lines exposed to increasing concentrations of glucose paralleled the response observed with insulin. GLP-1 mRNA was constitutively expressed by CMV/GLP-1 MIN-6 cells, and its expression was not controlled by glucose (FIGS. 3B and 3E). However, when the expression of GLP-1 was under the control of the rat insulin promoter (RIP/GLP-1), a significant glucose dependent expression of both insulin and GLP-1 genes was observed (FIGS. 3C and 3F).

Example 13

Glucose-Dependent Secretion of Insulin

Figure 4:
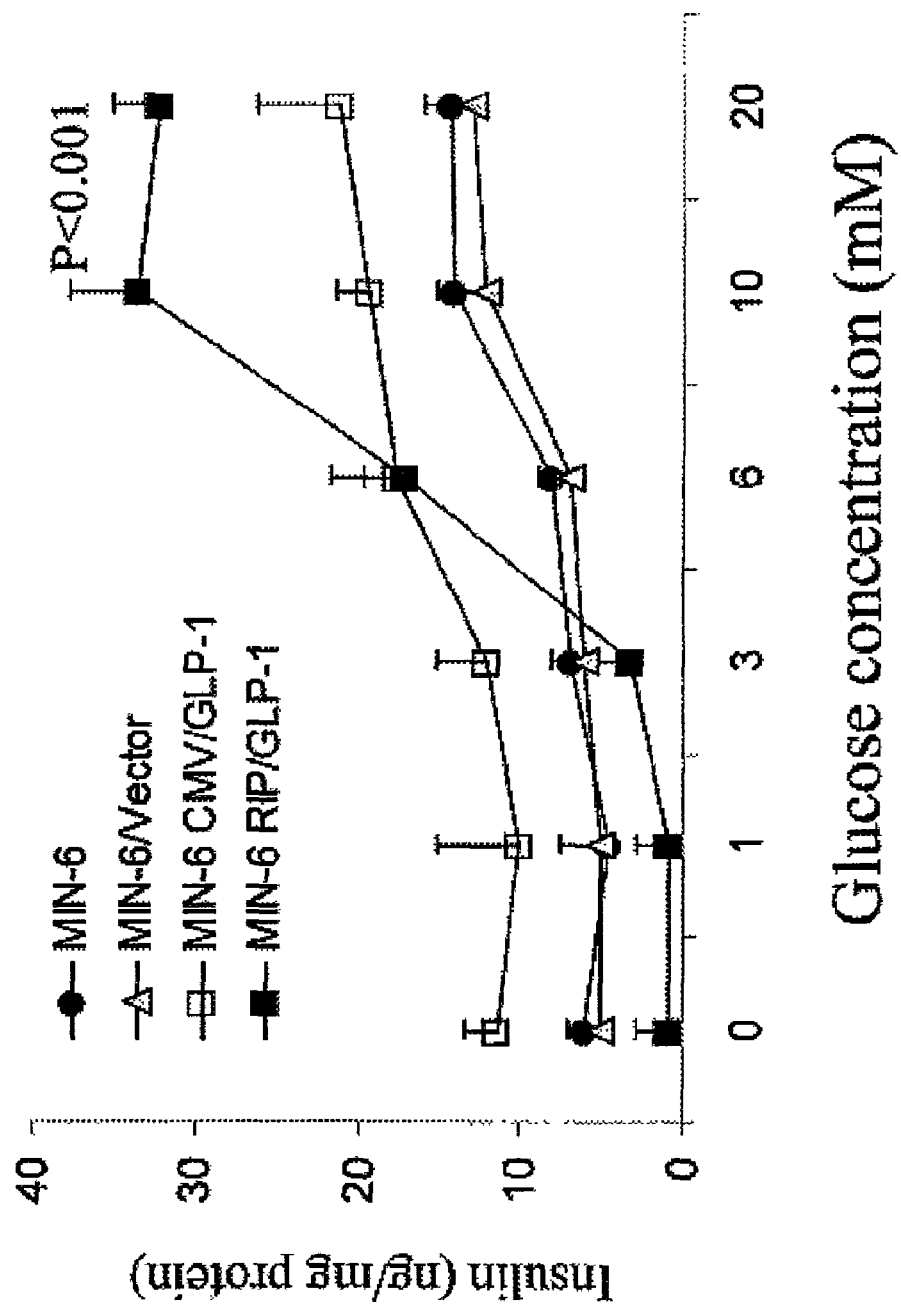
FIG. 4 graphically depicts a glucose-dependent insulin secretion in a culture medium. Insulin accumulation into the culture medium was determined after a 2-hour wash out period, carried out with serum-free and glucose-free medium. Parental MIN-6 cells, MIN-6 cells transfected with the vector alone, MIN-6 cells transfected with CMV/GLP-1, and MIN-6 cells transfected with RIP/GLP-1 were incubated in the presence of various concentrations of glucose for 8 hours. Each experiment was repeated at least four times and the data plotted on the graph represent the mean plus or minus one standard deviation. Insulin levels were normalized by the total protein level in each individual culture. Statistical significance of the data was evaluated by ANOVA.

CMV/GLP-1 cells, RIP/GLP-1 cells, parental MIN-6 cells, and cells transfected with the pSecTag2A plasmid alone, were cultured in the presence of increasing concentrations of glucose as described for northern blot analysis. Culture medium from various culture conditions was then collected and subjected to RIA for insulin and for protein assay to detect the total protein content in each medium sample. MIN-6 cells transfected solely with the pSecTag2A plasmid, as well as parental cells transfected with the GLP-1 construct under the CMV promoter, all showed a very similar glucose-dependent pattern of insulin secretion (FIG. 4). When the responsiveness to glucose at 3 mM and 20 mM was compared, the insulin levels in the culture medium were increased by 1.6% for parental cells, 1.5% for cells transfected with plasmid alone, and 1.7% for CMV/GLP-1 MIN-6 cells.

Cellular transfection with the RIP/GLP-1 construct promoted a profoundly different pattern of insulin secretion. In these cells, insulin secretion appeared to be strongly regulated by the concentration of glucose in the culture medium (FIG. 4). Insulin levels in the culture medium obtained from cells grown in the absence of glucose were significantly lower when compared to the other cell lines tested (i.e., parental, plasmid-transfected, and CMV/GLP-1 transfected ($p<0.05$)). Increasing the concentration of glucose in the culture medium induced a linear increase in the accumulation of insulin into the culture medium ($p<0.001$), such that in the presence of 20 mM glucose, insulin levels were approximately 10-fold greater than those observed in the presence of 3 mM glucose ($p<0.001$).

RIP/GLP MIN-6 cultured in the presence of the GLP-1 receptor antagonist Exendin-9 showed a significant reduction of the glucose-dependent secretion of insulin compared to cells transfected with the plasmid alone (FIG. 5). While in control cells grown in the presence of 10 mM glucose there was a 160% increase of insulin content into the culture medium within the first 30 minutes of culture, at the same time point the presence of Exendin-9 prevented the time dependent accumulation of insulin ($p<0.01$).

Example 14

Regulation of GLP-1 Secretion

Parental MIN-6 cells and cells transfected with the plasmid alone, cultured in the presence of various concentrations of glucose, did not secrete any detectable amount of GLP-1 (FIG. 6). Cellular transfection with human GLP-1 was associated with the secretion of the counterpart protein into the culture medium. However, a significant difference between the two GLP-1 transfected cell lines was observed. While the presence of the insulin promoter placed upstream to the GLP-1 coding sequence induced an increase in the GLP-1 accumulation into the culture medium in response to glucose ($p<0.001$), cells transfected with the GLP-1 gene driven by the CMV promoter exhibited a constitutive release of GLP-1, and this did not vary in response to ambient concentrations of glucose (FIG. 6).

Example 15

Immunofluorohistochemistry for IDX-1

MIN-6 (parental, CMV/GLP-1, RIP/GLP-1) cells were cultured for 12 hours in serum-free medium containing 0 mM, 6 mM or 12 mM glucose. Using anti-IDX-1 antibody, a positive immunoreactivity for IDX-1 was detected in all culture conditions (FIG. 7). Transfected cells (with either of the two GLP-1 constructs) showed a greater abundance of IDX-1 cytoplasmic protein levels when compared to parental MIN-6 cells. Exposure to greater concentrations of glucose appeared to further increase the expression level of IDX-1 in cells that were transfected with the CMV/GLP-1 construct (FIGS. 7D, 7E, and 7F).

A much greater glucose-dependent increase of IDX-1 was observed in cells transfected with the RIP/GLP-1 construct when exposed to different concentrations of glucose (FIGS.

7G, 7H, and 7I), when compared to either control or CMV/GLP-1 MIN-6 cells. Although a different degree of positivity for IDX-1 was present in all cell lines tested, the percentage of IDX-1-positive cells, the intensity of the staining for IDX-1, and the intracellular localization of IDX-1 (i.e., cytoplasmic vs. nuclear) varied significantly among the various cell and treatment groups. Of all cell lines studied, RIP/GLP-1 MIN-6 cells appeared to respond best to glucose. In those cultures, the number of cells positive for the nuclear localization of IDX-1 increased from 10±7% in the absence of glucose to 65±17% when exposed to 6 mM glucose, reaching 90±8% in the presence of 12 mM glucose (versus 10±4%, 18±12%, and 35±15% in parental cell culture in the presence of 0 mM, 6 mM and 12 mM glucose, respectively).

CMV/GLP-1 cells showed an intermediate level of response to glucose, between the values observed for parental cells and cells transfected with the RIP/GLP-1 construct. In the absence of glucose, 17±5% of cells showed a nuclear localization of IDX-1, increasing to 40±8% and to 55±11% in the presence of 6 mM and 12 mM glucose, respectively.

Example 16

Western Blot Analysis for GLP-1 Receptor

GLP-1 receptor (GLP-R) immunodetection was performed for MIN-6 cells transfected with the RIP/GLP-1 construct after culturing cells in the presence of various concentrations of glucose (0 mM, 3 mM, 6 mM, and 15 mM) for 12 hours. Western blot analysis was carried out with a monoclonal antibody that recognizes an epitope of the native protein located on the extracellular surface of human cells. A 62-kDa protein was detected in all culture conditions studied. No significant changes in GLP-1R protein levels were observed as a result of treatment with different concentrations of glucose (FIG. 8). This suggested that the glucose-dependent increase in GLP-1 levels (FIG. 4) was not associated with a down regulation of the protein levels of GLP-1 receptor (FIG. 8).

Example 17

Gel Shift Analysis

Figure 9:
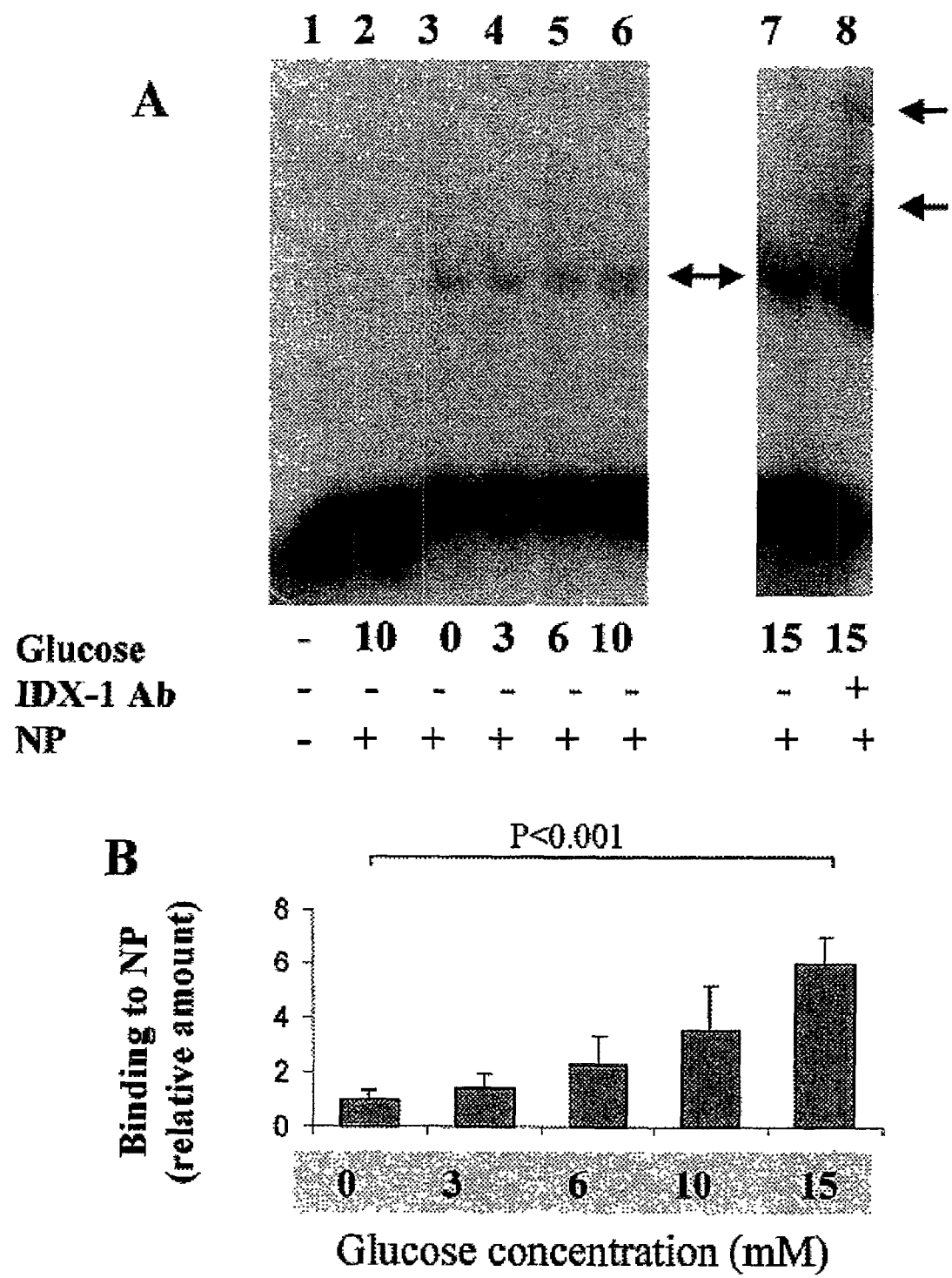
FIGS. 9A–B depict glucose- and GLP-1-dependent binding of IDX-1 to the rat insulin promoter A1 element. Nuclear extract from RIP/GLP-1 MIN-6 cells cultured in the presence of different concentrations of glucose were analyzed by electrophoretic mobility shift assays (EMSA) for binding to the A1 element of the insulin promoter $\gamma^{32}$P-labeled probe.

Increasing concentrations of glucose in the culture medium induced a linear increase in the binding of IDX-1 to the A1 element of the insulin promoter (FIG. 9). This glucose-dependent activation of the insulin promoter mirrored the glucose-dependent secretion of GLP-1. Control nuclear extracts from parental MIN-6 cells showed no increase in IDX-1 binding to the insulin promoter in response to glucose.

To confirm the specificity of IDX-1 binding, we performed a supershift analysis with an anti-IDX-1 antibody, in addition to a competition assay with unlabeled A1 oligonucleotide. The presence of the anti-IDX-1 antibody in the nuclear extracts induced a shift in the size of the detected band (FIG. 9, Lane 8), while the presence of unlabeled A1 oligonucleotide abolished the nuclear protein binding (FIG. 9).

Example 18

Inhibition of cAMP-Dependent Signaling Pathway

To investigate whether the observed glucose-dependent insulin synthesis and secretion of RIP/GLP-1 MIN-6 cells was mediated by a cAMP-dependent signaling pathway, cells were grown in the presence of Rp-cAMP. Cells and culture media were collected for northern blot analysis and RIAs. Determination of cAMP levels demonstrated that Rp-cAMP was capable of inhibiting cAMP accumulation (FIG. 10A). Accumulation of insulin in the culture medium was also inhibited by Rp-cAMP, suggesting that insulin secretion was entirely under the cAMP-dependent signaling pathway (FIG. 10B). Detection of insulin mRNA levels showed a very different pattern when compared with insulin secretion, suggesting that there was a dissociation between the mechanism(s) by which GLP-1 controls the secretion of insulin and its action at the transcription level of the insulin gene (FIG. 10C).

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method for constructing a glucose dependent insulin-secreting cell, in vitro, the method comprising the steps of:
providing an insulin-secreting cell, in vitro;
isolating from a proglucagon gene a minigene construct consisting of (a) the coding region for a protein selected from the group consisting of glucagon-like peptide-1 (GLP-1) and an analog of GLP-1, said analog of GLP-1 being further selected from the group consisting of SEQ ID NO. 1 and SEQ ID NO. 3; (b) a partial fragment of an IP sequence at the 5'-end; and (c) a nucleotide sequence at the 3'-end wherein the nucleotide sequence at the 3'-end is selected from the group consisting of, an entire IP-2 sequence and an entire IP-2 sequence along with a partial fragment of a glucagon-like peptide-2 (GLP-2) sequence;
operably linking a promoter to the minigene construct;
inserting or ligating the minigene construct into a plasmid; and
transfecting the plasmid into the insulin-secreting cell, whereby said insulin-secreting cell produces GLP-1 or an analog of GLP-1 in a glucose dependent manner.

2. The method of claim 1, wherein the protein is GLP-1.

3. The method of claim 2, wherein the GLP-1 is SEQ ID NO. 2.

4. The method of claim 1, wherein the promoter is selected from the group consisting of a human promoter that has a glucose-responsive element and an insulin promoter of an animal species.

5. The method of claim 1, wherein the promoter is selected from the group consisting of rat insulin II promoter (RIP) and rat insulin 7 promoter.

6. The method of claim 1, wherein the plasmid is a pSecTag2 plasmid, and the method further comprises deleting from the plasmid the cytomegalovirus (CMV) sequence.

7. The method of claim 6, wherein the minigene construct is inserted at the Hind-III and Pst-I sites of the plasmid.

8. A method for constructing a glucose-dependent insulin-secreting cell, in vitro, the method comprising the steps of:
providing an insulin-secreting cell, in vitro;
isolating from a proglucagon gene a minigene construct, SEQ ID NO: 6;
operably linking a promoter to the minigene construct;
inserting or ligating the minigene construct into a plasmid; and
transfecting the plasmid into the insulin-secreting cell, whereby said insulin-secreting cell produces GLP-1 or an analog of GLP-1 in a glucose-dependent manner.

9. The method of claim 8, wherein the promoter is selected from the group consisting of a human promoter that has a glucose-responsive element and an insulin promoter of an animal species.

10. The method of claim 8, wherein the promoter is selected from the group consisting of rat insulin II promoter (RIP) and rat insulin 7 promoter.

11. The method of claim 8, wherein the plasmid is a pSecTag2 plasmid, and the method further comprises deleting from the plasmid the cytomegalovirus (CMV) sequence.

12. The method of claim 11, wherein the minigene construct is inserted at the Hind-III and Pst-I sites of the plasmid.

13. An insulin-secreting cell, produced by a method comprising:
providing an insulin-secreting cell, in vitro;
isolating from a proglucagon gene a minigene construct consisting of (a) the coding region for a protein selected from the group consisting of glucagon-like peptide-1 (GLP-1) and an analog of GLP-1, said analog of GLP-1 being further selected from the group consisting of SEQ ID NO. 1 and SEQ ID NO. 3; (b) a partial fragment of an IP sequence at the 5'-end; and (c) a nucleotide sequence at the 3'-end wherein the nucleotide sequence at the 3'-end is selected from the group consisting of, an entire IP-2 sequence and an entire IP-2 sequence along with a partial fragment of a glucagon-like peptide-2 (GLP-2) sequence;

operably linking a promoter to the minigene construct;

inserting or ligating the minigene construct into a plasmid; and transfecting the plasmid into the insulin-secreting cell, whereby said insulin-secreting cell produces GLP-1 or an analog of GLP-1 in a glucose dependent manner.

14. The insulin-secreting cell of claim 13, wherein the protein is GLP-1.

15. The insulin-secreting cell of claim 14, wherein the GLP-1 is SEQ ID NO. 2.

16. The insulin-secreting cell of claim 13, wherein the promoter is selected from the group consisting of a human promoter that has a glucose-responsive element and an insulin promoter of an animal species.

17. The insulin-secreting cell of claim 13, wherein the promoter is selected from the group consisting of rat insulin II promoter (RIP) and rat insulin 7 promoter.

18. The insulin-secreting cell of claim 13, wherein the plasmid is a pSecTag2 plasmid, and the method further comprises deleting from the plasmid the cytomegalovirus (CMV) sequence.

19. The insulin-secreting cell of claim 18, wherein the minigene construct is inserted at the Hind-III and Pst-I sites of the plasmid.

20. An insulin-secreting cell, produced by a method comprising:

providing an insulin-secreting cell, in vitro;

isolating from a proglucagon gene a minigene construct consisting of SEQ ID NO: 6;

operably linking a promoter to the minigene construct;

inserting or ligating the minigene construct into a plasmid; and transfecting the plasmid into the insulin-secreting cell, whereby said insulin-secreting cell produces GLP-1 or an analog of GLP-1 in a glucose-dependent manner.

21. The insulin-secreting cell of claim 20, wherein the promoter is selected from the group consisting of a human promoter that has a glucose-responsive element and an insulin promoter of an animal species.

22. The insulin-secreting cell of claim 20, wherein the promoter is selected from the group consisting of rat insulin II promoter (RIP) and rat insulin 7 promoter.

23. The insulin-secreting cell of claim 20, wherein the plasmid is a pSecTag2 plasmid, and the method further comprises deleting from the plasmid the cytomegalovirus (CMV) sequence.

24. The insulin-secreting cell of claim 23, wherein the minigene construct is inserted at the Hind-III and Pst-I sites of the plasmid.

* * * * *